United States Patent [19]

Iván et al.

[11] Patent Number: 5,073,381
[45] Date of Patent: Dec. 17, 1991

[54] AMPHIPHILIC NETWORKS

[75] Inventors: Béla Iván; Joseph P. Kennedy; Paul W. Mackey, all of Akron, Ohio

[73] Assignee: University of Akron, Akron, Ohio

[21] Appl. No.: 537,508

[22] Filed: Jun. 13, 1990

Related U.S. Application Data

[63] Continuation-in-part of Ser. No. 232,444, Aug. 15, 1988, Pat. No. 4,942,204.

[51] Int. Cl.$^5$ .............................. A61K 9/14
[52] U.S. Cl. ..................... 424/487; 525/293
[58] Field of Search .............. 424/487, 81; 525/293

[56] References Cited

U.S. PATENT DOCUMENTS

| | | | |
|---|---|---|---|
| 4,548,990 | 10/1985 | Mueller et al. | 528/123 |
| 4,575,539 | 3/1986 | DeCrosta et al. | 525/283 |
| 4,649,043 | 3/1987 | Urquhart et al. | 424/469 |
| 4,666,704 | 5/1987 | Shalati et al. | 424/19 |
| 4,693,887 | 9/1987 | Shah | 424/19 |
| 4,764,380 | 8/1988 | Urquhart et al. | 424/465 |
| 4,824,678 | 4/1989 | Lindahl et al. | 424/473 |
| 4,840,796 | 6/1989 | Sweet et al. | 424/448 |
| 4,851,232 | 7/1989 | Urquhart et al. | 424/469 |
| 4,857,313 | 8/1989 | Song et al. | 424/81 |
| 4,857,334 | 8/1989 | Korol et al. | 424/445 |
| 4,873,086 | 10/1989 | Good | 424/409 |
| 4,931,287 | 6/1990 | Bae | 424/484 |

Primary Examiner—Thurman K. Page
Assistant Examiner—D. Gabrielle Phelan
Attorney, Agent, or Firm—Oldham & Oldham Co.

[57] ABSTRACT

New controlled and/or sustained drug release amphiphilic compositions based on various amphiphilic networks of the present invention are described. New processes for manufacturing amphiphilic networks are also described. These new processes allow for the production of more diverse amphiphilic networks. The controlled and/or sustained drug release properties of the networks of the present invention show release controlled and sustained release profiles for 20 hours or more and Fickian and non-Fickian diffusion rates.

16 Claims, 13 Drawing Sheets

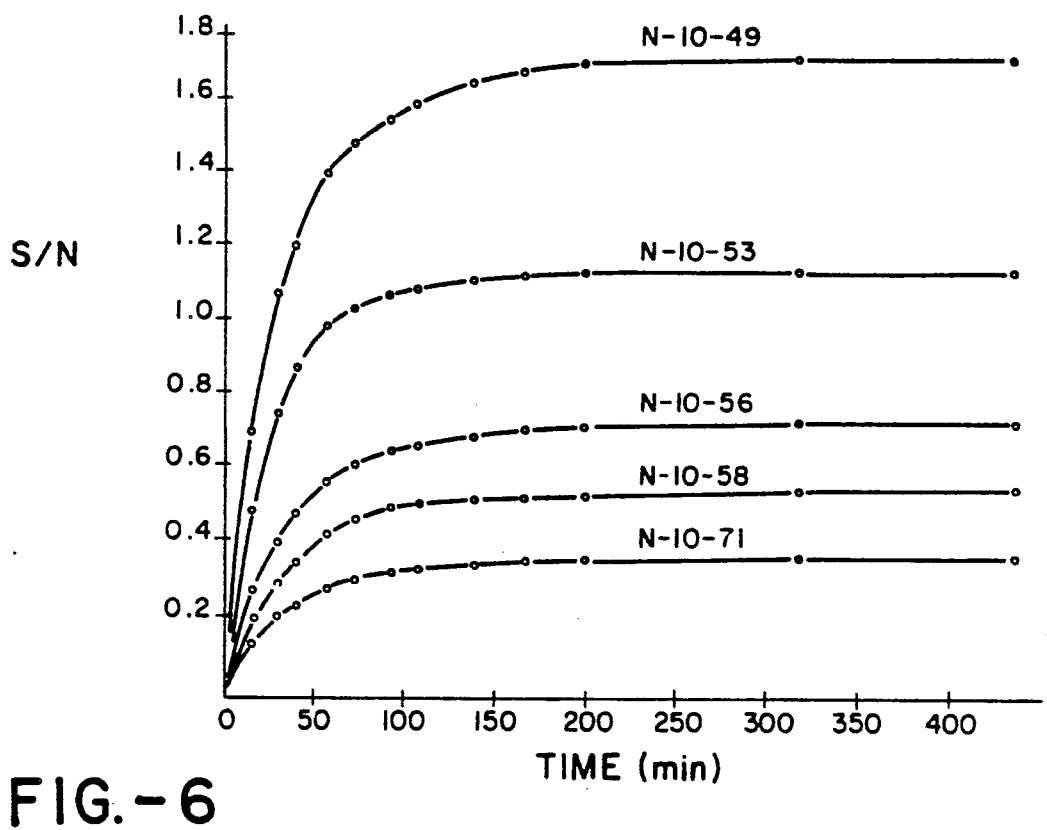
FIG.-6
FIG.-7
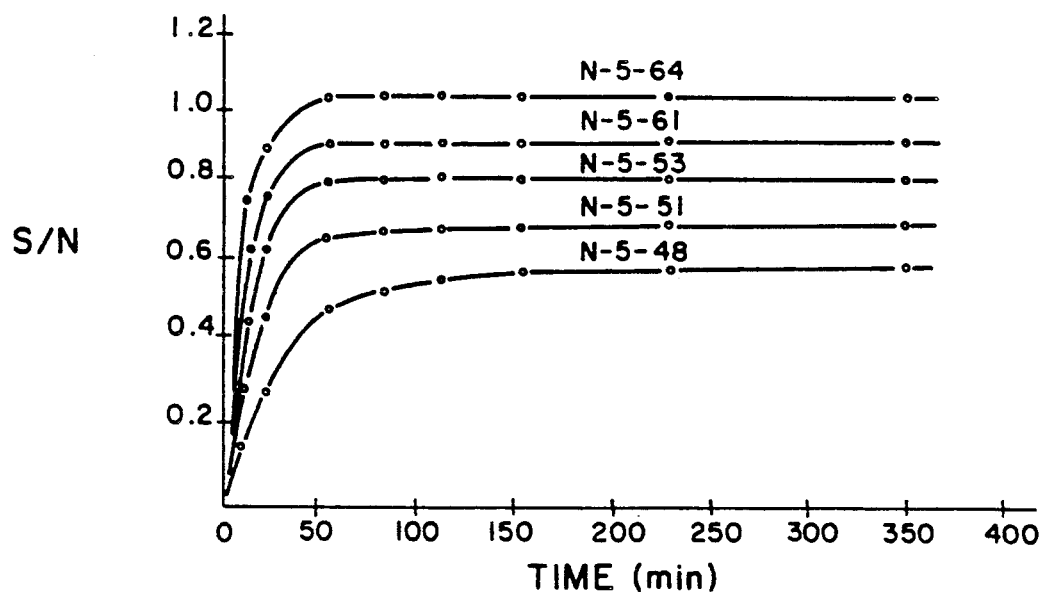

AMPHIPHILIC NETWORKS

This invention was made in the course of research that was supported by National Science Foundation (NSF) Grant DMR-84-18617.

This is a continuation-in-part of U.S. patent application Ser. No. 07/232,444 filed Aug. 15, 1988 and now U.S. Pat. No. 4,942,204.

TECHNICAL FIELD

This invention relates to amphiphilic polymer networks having hydrophobic polyolefin segments and hydrophilic segments and to a method to preparing the same. More particularly, this invention relates to amphiphilic polymer networks in which mechanical properties and swellability in hydrophilic and hydrophobic solvents can be varied over a wide range by variation of the relative amounts of hydrophobic monomer portion and hydrophilic monomer portion. This invention also relates to a controlled and/or sustained drug release composition based on the amphiphilic polymer networks of this invention. Furthermore, the invention relates to a novel process of making amphiphilic networks by first blocking a monomer with a blocking agent to alter the monomer's solubility and/or compatibility properties, followed by polymerizing the blocked monomer with a second compatible monomer to form a compatible network which, upon deblocking, converts the network into the desired amphiphilic network.

BACKGROUND ART

An amphiphilic polymer network is a random assemblage of hydrophilic and hydrophobic polymer chains that is able to swell in both hydrophilic solvents (e.g., water) and hydrophobic solvents (e.g., a liquid hydrocarbon). Amphiphilic polymer networks are described for example, in U.S. Pat. No. 4,486,572 to Kennedy (one of the applicants herein), and in Keszler and Kennedy, *Journal of Macromolecular Science*, Chemistry Edition, Vol. A21, No. 3, pages 319-334 (1984).

U.S. Pat. No. 4,085,168 to Milkovich et al. describes chemically joined, phase-separated, self-cured hydrophilic thermoplastic graft copolymers which are copolymers of at least one hydrophilic (water soluble) ethylenically unsaturated monomer or mixture thereof and at least one copolymerizable hydrophobic macromolecular monomer having an end group which is copolymerizable with the hydrophilic monomer. The resulting copolymer is a graft copolymer characterized as having a comb-type structure consisting of a hydrophilic backbone polymer with hydrophobic polymer side chains bonded thereto. The side chains are disclosed as being bonded to the hydrophilic polymer at only one end of the side chain, so that no network results.

DISCLOSURE OF THE INVENTION

This invention, according to one aspect, provides a novel amphiphilic copolymer composition comprising a network having hydrophobic segments and hydrophilic segments.

The network can be in the form of hydrophilic polymer segments or chains crosslinked by bifunctional hydrophobic polymer segments, or chains or hydrophobic polymer segments, or chains crosslinked by bifunctional hydrophilic polymer segments, or hydrophilic and hydrophobic polymer segments crosslinked by a crosslinking agent. The amphiphilic network may have two glass transition temperatures indicating a phase-separated domain structure and is swellable but insoluble in both water and n-heptane. These amphiphilic networks have various biomedical applications.

This invention, according to another aspect, provides a process for preparing an amphiphilic polymer network as described above, wherein a (meth)acryloyl-capped polyolefin is copolymerized with a class of hydrophilic acrylate monomers under free radical polymerization conditions.

This invention, according to another aspect, provides a novel drug control release composition comprising an amphiphilic network as described above, wherein a pharmalogically active agent or ingredient is deposited within the network to afford controlled and/or sustained release of the pharmalogically active agents when placed in contact with body fluids.

According to another aspect of this invention, a novel process for making amphiphilic networks is provided, comprising polymerizing a first and second monomer which are incompatible, where the first monomer has been treated with a removable blocking agent to transform it into a blocked monomer having solubility and compatibility properties similar to the second monomer. The polymerization results in the formation of a compatible network which can then be converted into an amphiphilic network by deblocking the blocked monomer which restores the first monomer's incompatibility with the second monomer.

More generally, a process is described whereby an amphiphilic network can be made from a crosslinked, compatible copolymer network by chemically transforming one polymer of the copolymer network into a polymer having opposite or nearly opposite solubility and/or compatibility properties.

BRIEF DESCRIPTION OF THE DRAWINGS

FIGS. 5 and 6 are swelling curves of representative amphiphilic networks of this invention in water at room temperature.

FIGS. 7 and 8 are swelling curves of representative amphiphilic networks of this invention in n-heptane at room temperature.

BEST MODE FOR CARRYING OUT THE INVENTION

Figure 1:
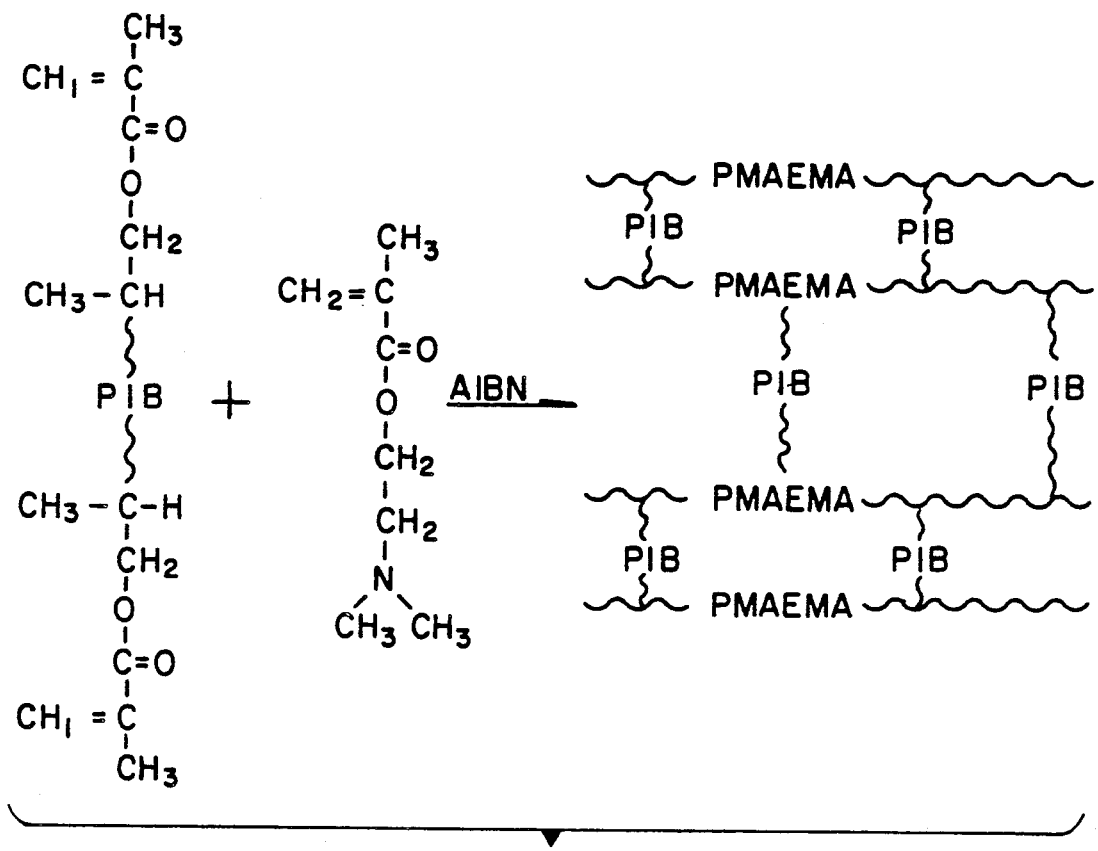
FIG. 1 is a schematic representation of a preferred amphiphilic polymer network of this invention and the reaction involved in its synthesis.

This invention will be described with particular reference to synthesis of amphiphilic networks from methacryloyl-capped polyisobutylene (the hydrophobic macromolecular monomer) (MA-PIB-MA) and polyacrylates such as N,N-dimethylacrylamide (DMAAm) and 2-hydroxyethyl methylmethacrylate (HEMA), which constitutes the best mode and preferred embodiment of this invention.

This invention will also describe the use of these amphiphilic networks in controlled and/or sustained drug release compositions with the ability to vary the drug retention or drug release time depending on the composition of the network.

This invention will also describe the synthesis of an amphiphilic network which utilizes a bifunctional hydrophilic macromonomer and a hydrophobic monomer which is blocked by removable blocking which converts the hydrophobic monomer into a hydrophilic monomer to facilitate polymerization and network formation. The resulting network can then be treated to affect a deblocking of the blocked monomer thus giving rise to the desired amphiphilic network.

Starting materials for preparation of amphiphilic networks of this invention are (a) a hydrophobic acryloyl or methacryloyl-capped polyolefin and (b) a hydrophilic ω (di-alkylamino) lower alkylacrylate or methacrylate or a hydrophilic dialkylacrylamide or methacrylamide or a hydrophilic ω hydroxy alkylacrylate or methacrylate.

The hydrophobic methacryloyl-capped polyolefin is a bifunctional macromolecular monomer or, more simply, a macromonomer which may be represented by the following formula (I)

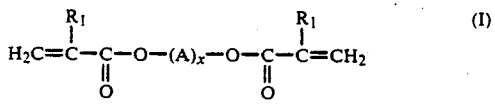
(I)

where A is a divalent unit derived from an olefin having four to about twelve carbon atoms or a mixture thereof and $R_1$ is hydrogen or methyl and x is the degree of polymerization of the macromonomer represented by formula (I).

The macromonomer (I) is a linear polyolefin having a number average molecular weight $M_n$ of at least about 500, preferably from about 2,000 to about 50,000, more preferably from about 4,000 to about 12,000; a degree of polymerization x corresponding to this $M_n$ (i.e, x is from about 35 to about 100) and a molecular weight distribution $M_w/M_n$ from about 3.0 to about 1.1; capped at both ends with acryloyl or methacryloyl groups. Synthesis of the preferred macromonomer (I), i.e., methacryloyl-capped polyisobutylene is described in J. P. Kennedy and M. Hiza, *Polymer Bulletin.* Vol. 10, pages 146-151 (1983).

Other macromonomers of the formula (I) may be prepared by an analogous method, substituting acrylate for methacrylate ester and/or substituting another olefin having 4 to 12 carbon atoms, preferably another alpha mono-olefin such as 1-butene, 3-methyl-1-butene, styrene, etc., for isobutylene.

The hydrophilic comonomer segment is derived from a monofunctional monomer or mixture thereof that is copolymerizable with the acryloyl or methacryloyl end groups of the hydrophobic acryloyl or methacryloyl capped polyolefin and which yields a water soluble segment when homopolymerized. Preferred hydrophilic polyacrylate segments are those derived from acrylate monomer of formulas (II), (III), and (IV) as shown below:

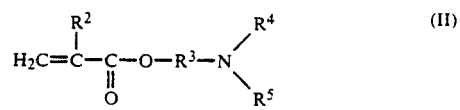
(II)

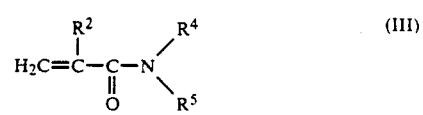
(III)

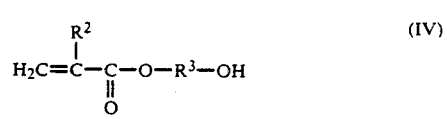
(IV)

where $R^2$ is hydrogen or methyl, $R^3$ is an alkylene group of 2 to about 4 carbon atoms, and $R^4$ and $R^5$ may be the same or different and each is hydrogen or an alkyl radical of 1 to about 4 carbon atoms.

The preferred acrylate of the formula (II) is 2-(dimethylamino)ethyl methacrylate (DMAEMA). The preferred acrylates of formulas (III) and (IV) for controlled and/or sustained drug release networks are N,N-dimethylacrylamide (DMAAm) and 2-hydroxyethyl methacrylate (HEMA), respectively.

Other suitable hydrophilic comonomers include N-vinyl pyrrolidone, acrylamide and other similar hydrophilic acrylates or methacrylates.

Preferably the hydrophobic macromonomer (I) and the hydrophilic comonomer have the same ester group, which is preferably methacryloyl, so that the amphiphilic polymer network which is formed will be a random copolymer.

The weight ratio of hydrophobic macromonomer to hydrophilic comonomer is generally in the range of about 80:20 to about 20:80, preferably about 70:30 to about 30:70, most preferably from about 60:40 to about 40:60.

Copolymerization of the hydrophobic macromonomer with the hydrophilic comonomer is carried out under conventional free radical polymerization conditions, in a suitable organic solvent such as tetrahydrofuran, methylene chloride, benzene, or heptane, at a temperature from about 40° to about 90° C., for a time sufficient to achieve the desired degree of cross-linking and to consume most of at least one of the two monomers (typically about 3 days at 60° C. will achieve the desired copolymerization), in the presence of a free radical initiator such as azobis(isobutylronitrile) (AIBN), cumyl peroxide, or tert.-butylhydroperoxide. This reaction is shown in FIG. 1, which gives the preferred reactants, i.e., methacryloyl-capped polyisobutylene (MA-PIB-MA) (formula I-a) and dimethylaminoethyl methacrylate (DMAEMA) (formula II-a) and the preferred initiator (AIBN) by way of example.

When the reaction is complete, the reaction product may be cooled to ambient temperature and may be extracted sequentially with a non-polar organic solvent (e.g., n-hexane), a polar organic solvent (e.g., ethanol) and water to remove unreacted hydrophobic macromonomer (e.g., MA-PIB-MA), unreacted hydrophilic comonomer (e.g., DMAEMA) and hydrophilic homopolymer (e.g., poly(dimethylaminoethyl)methacrylate homopolymer), which may be represented either as PDMAEMA or PMAEMA. This leaves an amphiphilic polymer network according to the invention. This amphiphilic polymer network is shown schematically in FIGS. 1 and 1A. This network consists of hydrophilic chains (of PMAEMA, for example) which are connected to hydrophobic chains (e.g., of MA-PIB-MA) which constitute the cross-linking agent at trifunctional cross-link points.

Figure 1A:
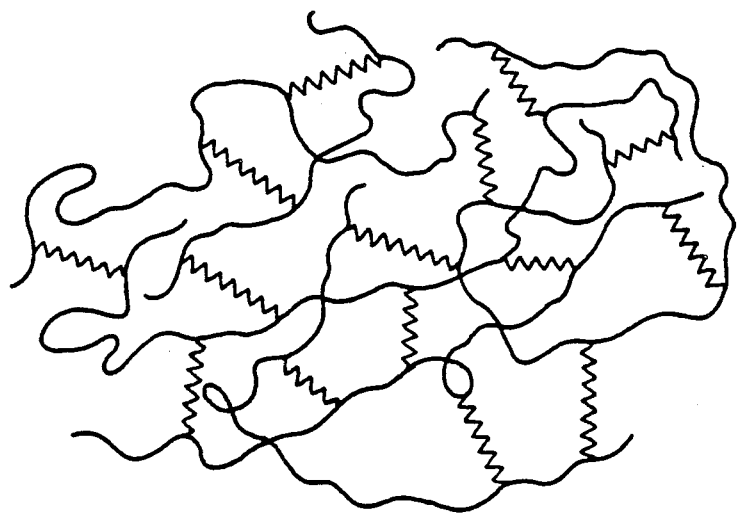
FIG. 1A is a further schematic representation of an amphiphilic polymer network of this invention.

In FIG. 1A, the hydrophilic chains are represented by smooth, curved lines and the hydrophobic chains are represented by wavy lines. As may be seen in FIG. 1A, the hydrophilic polymer chains are for the most part linear although some branching does occur.

Amphiphilic polymer networks of this invention may have hydrophobic macromonomer contents ranging from about 40% to about 80% by weight, preferably from about 45% to about 75% by weight, based on total polymer content (which is the sum of hydrophobic macromonomer and hydrophilic polymerized acrylate or methacrylate). The preferred amphiphilic polymer network consists essentially of about 40% to about 80% by weight, preferably about 45% to about 75% by weight of MA-PIB-MA, with balance being poly[2-(dimethylaminoethyl) methacrylate] (PDMAEMA or PMAEMA); the latter being the hydrophilic component and the former being the hydrophobic component.

Differential scanning calorimetry (DSC) shows the existence of two glass transition temperatures in these networks, indicating a phase-separated domain structure.

The average molecular chain length M of the hydrophilic polymer chain (i.e., PDMAEMA) between two crosslinked sites may vary over a wide range, from about 1,000 and up, typically from about 1,200 to about 6,000, depending on the weight percentage of hydrophobic macromonomer units (i.e., MA-PIB-MA) in the network and the number average molecular weight $M_n$ of these macromonomer units. The $M_c$ of hydrophilic chain increases with increasing $M_n$ value of the hydrophobic macromer and with decreasing weight ratio of hydrophobic macromer to hydrophilic monomer in the reactant charge. The $M_c$ values for hydrophilic polymer chains herein are calculated on the assumption that all of the hydrophobic macromer is incorporated into the amphiphilic polymer network, an assumption which is not always correct, particularly at higher hydrophobic macromer/hydrophilic monomer charge weight ratios. The average molecular chain length, or $M_c$, value for the hydrophobic macromer is assumed to be the same as the $M_n$ value of the hydrophobic macromer.

Amphiphilic polymer networks of this invention are swellable in both water (and other polar solvents) and n-heptane (and other non-polar solvents), but are not soluble in either. Solvent swelling of the preferred networks (MA-PIB-MA/PDMAEMA) ranges from about 170% to about 20% in water and from about 40% to about 170% in n-heptane with increasing MA-PIB-MA content. (The maxima and minima indicate the percentage swelling in networks containing 48% and 71.5%, respectively of MA-PIB-MA.)

Networks according to this invention in which the hydrophobic macromonomer is based on an olefin other than isobutylene, and/or in which the hydrophilic polymer chains are based on a monomer other than DMAEMA, exhibit about the same swellability in both water and n-heptane as do the preferred amphiphilic polymer networks.

Tensile strength and elongation in amphiphilic networks of this invention are controllable. Tensile strength typically varies from about 35 kg/cm$^2$ to about 60 kg/cm$^2$ and elongation typically varies from about 160% to about 210%, the former decreasing and the latter increasing with increasing hydrophobic macromer content. By way of illustration, the preferred MA-PIB-MA/DMAEMA networks exhibited tensile strength varying from 57.7 kg/cm$^2$ to 39.8 kg/cm$^2$ (at MA-PIB-MA contents of 48% and 71.5%, respectively) and elongations of 168% to 200% (also at MA-PIB-MA contents of 48% and 71.5%, respectively).

The amphiphilic polymer networks of this invention are hydrogels which, in the hydrated state, are structurally similar to natural tissue. As a result, these materials find use for various biomedical applications. These networks may be used for controlled drug release devices, implants for enzyme immobilization, artificial arteries, blood-contacting applications, various implantable reservoirs for drugs and metabolites for veterinary and human applications. For biomedical applications the preferred hydrophobic macromonomer content (e.g., MA-PIB-MA) is from about 53% to about 58% by weight, based on total polymer weight.

Networks of this invention may be cast into thin films and into various shapes.

A new process for the formation of amphiphilic networks has also been devised. In the past, network formation using a hydrophobic and a hydrophilic monomer has presented synthetic difficulties. These difficulties arise because of the differences in solubility and/or compatibility and reactivity of the two different types of monomers. These difficulties can, to a large extent, be overcome by disguising one of the monomers so that the two monomers behave similarly in the polymerization medium to facilitate more efficient co-polymerization.

A monomer can be disguised by reacting either a hydrophobic or hydrophilic monomer with a removable blocking agent which essentially converts the monomer into its opposite. That is, a hydrophilic monomer can be converted into a hydrophobic monomer by reacting the monomer with an appropriate removable blocking agent, thereby allowing the blocked or disguised monomer to be reacted with a second hydrophobic monomer. Conversely, a hydrophobic monomer can be converted into a hydrophilic monomer by reacting the monomer with an appropriate removable blocking agent reacted with a hydrophilic monomer. Once the network is formed, the removable blocking agent can be removed by appropriate chemical methods yielding the desired amphiphilic network.

More generally, this process can be envisioned as a chemical transformation of a compatible, blocky, copolymer network into an amphiphilic network. This conversion or transformation can be affected by chemically converting or transforming one polymer block into a polymer block having opposite or near opposite solubility and/or compatibility properties. Thus, a blocky or somewhat blocky, copolymeric, compatible network can be transformed into an amphiphilic network by merely effecting a chemical transformation of one of the copolymer blocks into an incompatible derivative of the block.

The chemical transformation can be any chemical transformation that will affect the desired conversion or transformation of one segment of a polymer network into an incompatible derivative. One such transformation could be a the protonation of a tertiary amine or amide which will convert a hydrophobic segment into a hydrophilic segment. The transformation can be, and preferably is accomplished on the network in a swollen state and thus can be thought of as quantitative derivatization of a compatible copolymeric network into an amphiphilic network.

The process comprises the steps of swelling a compatible, blocky, copolymeric, crosslinked network in a solvent and converting one block of said network into a block having opposite or nearly opposite compatibility properties whereby an amphilic network is formed. The compatible network can be of any form including a copolymer of a bifunctional macromonomer and a standard comonomer, two bifunctional macromonomers or two standard monomers and a crosslinking agent. The term "standard monomer" is used to refer to all typical monofunctional monomers such as acrylated, styrene and styrene derivatives, and all other polymerizable mono olefins and all polymerizable conjugated and non-conjugated diene monomers. Crosslinking agents include but are not limited to di and polyvinyl benzene and their derivatives, difunctional acrylates, and other similar crosslinking agents known in the art.

These procedures represent a significant improvement for manufacturing wider and more diverse types of amphiphilic networks from starting materials that are or would be, in many respects, incompatible and chemically very different in behavior and response to different environments and thus, give rise to networks without an amphiphilic characteristics or be unable to be copolymerized.

As an example of the blocking-deblocking process, HEMA (a hydrophilic methacrylate) can be converted to a hydrophobic methacrylate by reacting HEMA with the removable blocking agent trimethylsilyl chloride (TMS-Cl) to yield 2-(trimethylsiloxy)ethyl methacrylate (TMSHEMA) as shown below:

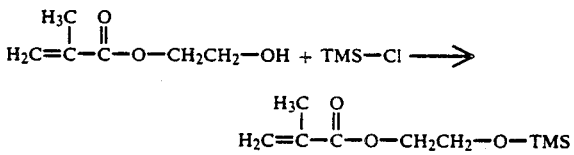

Once the disguised HEMA has been prepared, the monomer can be reacted with the hydrophobic methacrylate capped polyisobutylene monomer (MA-PIB-MA) to yield a hydrophobic network which then can be swollen in a 5% hydrochloric acid 2-methoxyethanol solution which causes hydrolysis of the trimethylsiloxy group back to the hydroxy group. The hyrdrolysis converts the initially formed network into the desired amphiphilic network where the hydrophobic part of the network is represented by polyisobutylene and the hydrophilic part of the network is represented by HEMA. Thus, a hydrophilic monomer is converted into a hydrophobic monomer and polymerized with MA-PIB-MA to form a hydrophobic network which is then converted to an amphiphilic network by treating the swollen network with a deblocking agent. The deblocking agent can be any chemical reagent utilized by one of ordinary skill in the art of synthetic chemistry for reversibly converting a given monomer into a physically and chemically near opposite of itself.

This same process will work equally well by polymerizing a hydrophilic telechelic macromonomer with a disguised hydrophobic comonomer where the disguised hydrophobic comonomer is produced by blocking a hydrophobic monomer with a removeable blocking agent which converts the hydrophobic monomer into a blocked monomer having hydrophilic characteristics. Thus, a hydrophilic macromonomer of formula (V)

Y—PEO—Y  (V)

where Y is selected from the representative and illustrative group consisting of an acrylate, a methacrylate, a styryl group or other similar polymerizable group and where PEO represents a polyethyleneoxide segment having a molecular weight $M_n$ of at least about 200, preferably from about 2,000 to about 50,000, more preferably from about 4,000 to about 12,000, can be reacted with a salt form of N,N-dialkyl-4-vinyl benzylamide.

The salt form of N,N-dialkyl-4-vinyl benzylamide is easily made by treating the benzylamide with a strong acid such as HCl, $H_2SO_4$, or other strong acids. Once the hydrophilic network is prepared, the network can be swollen in an appropriate hydrophilic solvent and treated with a base (the deblocking agent) such as an alkali hydroxide or other similar base which will convert the hydrophilic benzylamide salt into the hydrophobic benzylamide parent compound. Upon deblocking, the hydrophilic network is converted into an amphiphilic network. Compounds of formula (V) can be readily prepared by reacting poly(ethylene glycol) of a desired $M_n$ with acryloyl chloride or other acrylate or methacrylate reagent used for preparing acrylate or methacrylate esters of the poly(ethylene glycol). This technique is well known in the art.

This technique can be generally applied to a wide variety of systems where the monomers have reactive groups that will allow them to be converted from their inherent either hydrophobic or hydrophilic state, into a disguised essentially opposite state. The conversion will make polymerization of the blocked monomer more efficient and effective with monomers that are chemically and physically similar to the disguised or blocked monomer.

Thus, the new process involves the steps of:

1) blocking a first monomer with a removable blocking agent which converts said first monomer into a blocked first monomer, said blocked first monomer having opposite or nearly opposite solubility and/or compatibility properties compared with said first monomer;

2) polymerizing said blocked first monomer with a second monomer in a solvent and in the presence of a polymerization initiator and in the presence or absence of a crosslinking agent at a temperature, pressure and time sufficient to achieve polymerization, where said blocked first monomer and said second monomer have similar solubility and/or compatibility properties, whereby a network is formed; and 3) deblocking said blocked first monomer within said network by contacting said network with a deblocking agent in a solvent whereby said network is converted into said amphiphilic network.

This new process, when carried out in the absence of a crosslinking agent, requires one of the monomers to act as a crosslinking agent as is the case with the above example, where MA-PIB-MA is both the hydrophobic monomer and crosslink agent. However, a blocked monomer and a second monomer can also be polymerized in the presence of a crosslink agent to yield a crosslinked network. The only requirement in this latter system, to insure the formation of an amphiphilic network, is that the polymerization would have to be blocky or somewhat blocky in nature. That is, copolymer segments of sufficient size would have to be produced during polymerization so that when deblocking occurs, the transformed network would show differential solubility and amphiphilic behavior could be expressed.

Figure 12:
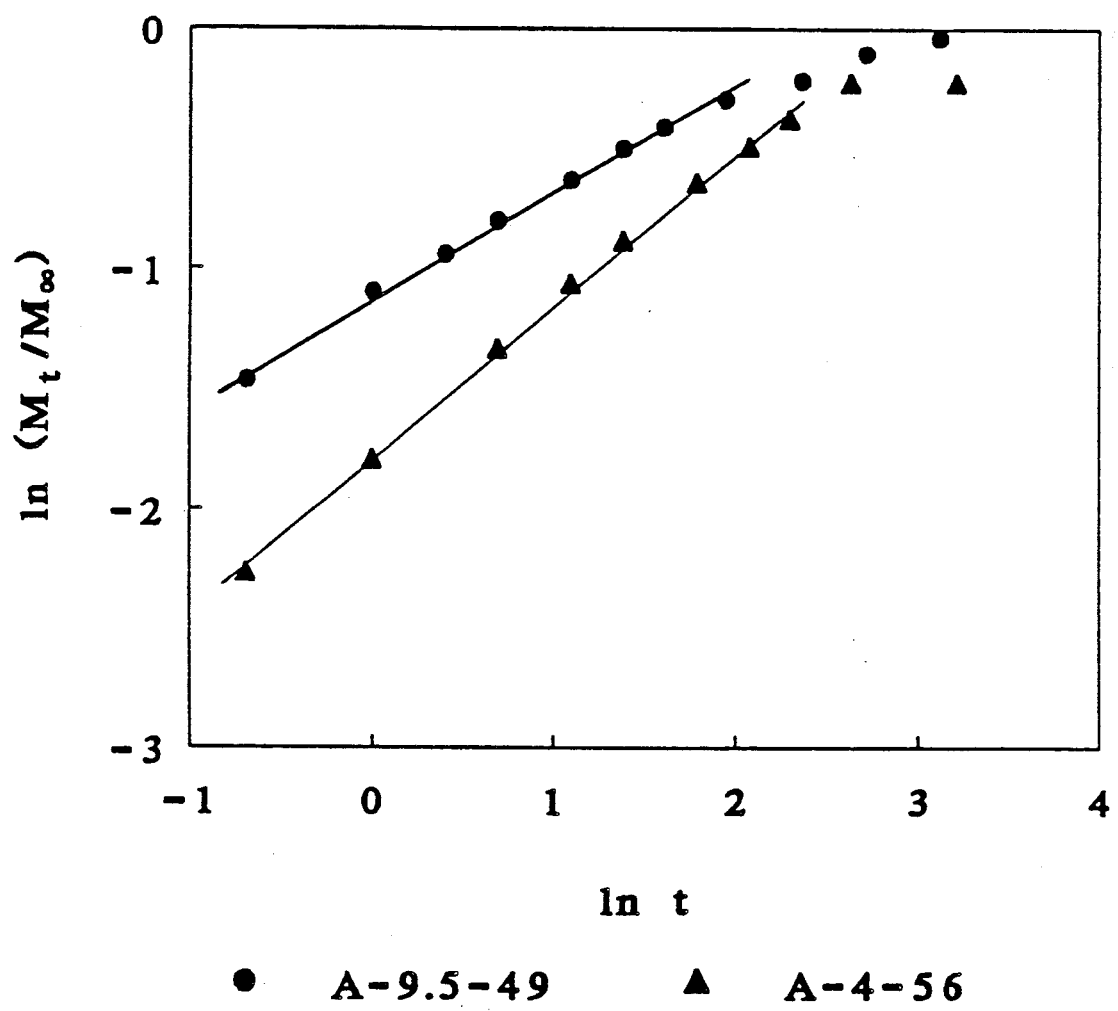
FIG. 12 is a log-log plot of the release profile of FIG. 11, showing the effect that hydrophobic monomer molecular weight has on the release of the theophylline.
Figure 16:
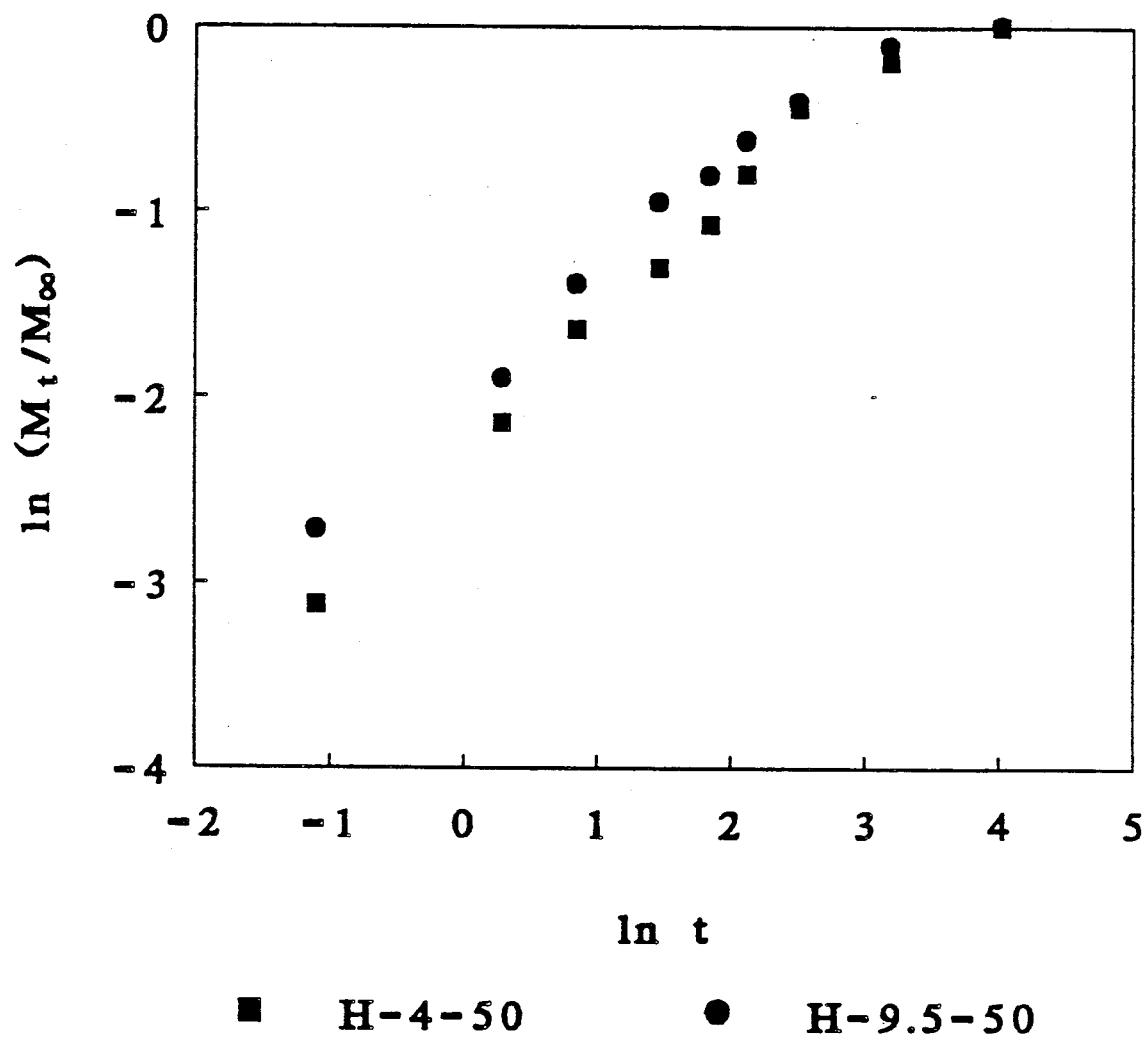
FIG. 16 is a log-log plot of the release profile of FIG. 13, showing the effect that hydrophobic monomer molecular weight has on the release of the theophylline.

The networks of this invention can be used for the controlled and/or sustained release of pharmacologically active ingredients or agents. These agents can either be water soluble, semi water soluble or water insoluble. Since the networks of the present invention are swellable in water, polar organic solvents and nonpolar organic solvents, a very wide spectrum of drugs and/or pharmacologically active agents can be deposited into the networks. The release rate can be controlled by the ratio of the amount of hydrophobic segments to the amount of hydrophilic segments in the network. This control criterion is shown in FIGS. 12 and 16 which show that the rate of drug delivery is controlled to some extent by the nature of the network, in that the diffusion rate for the networks A-4-56 and H-4-50 have different slopes than A-9.5-49 and H-9.5-50. The A-4 and A-9.5 differ essentially only in the molecular weight of the MA-PIB-MA used to make the networks. A-4 used a MA-PIB-MA of $M_n=4,000$ and A-9.5 used a MA-PIB-MA of $M_n=9,500$. Thus, a water soluble drug component can be deposited inside the network by swelling the network in an aqueous media containing the pharmaceutical agent. A water semi-soluble drug can be deposited inside the networks by swelling the network in an appropriate polar organic solvent containing the agent. Finally, a water insoluble or slightly soluble drug can be deposited inside the network by swelling the network in a non-polar organic solvent containing the agent.

The rate of release of an agent impregnated or otherwise deposited in the networks of the present invention can be estimated according to the following equation:

$$M_t/M_w = kT^n \qquad (i)$$

where $M_t$ is the amount of agent released at a given time (t), and $M_w$ is the total amount of agent released ($M_w$ should equal the total amount deposited in the network), k is a rate constant and n is an exponential factor. The exponential factor n is indicative of the release kinetics. When $n=0.5$ then pure Fickian diffusion is in operation. When $n=1.0$ then the diffusion obeys zeroth order kinetics.

The networks of the present invention possess n values ranging from about 0.4 to about 1.0. The deviation from pure Fickian diffusion, i.e., $n<0.5$ is due to the approximate nature of equation (i). Thus, the networks are capable of controlled release of agents, up to and beyond a 25 hour period of time. In fact, the HEMA networks described in Example 12 show release past 25 hours because FIG. 15 indicates that total release has not occurred at the 25 hour data point. The DMAAm networks show a near quantitative release at the 25 hour data point. However, networks of the present invention can be prepared which have release times less than 25 hours by simply changing the composition of the network. Increasing the hydrophilic portion of the amphiphilic networks will result in faster release, while decreasing the hydrophilic portion of the amphiphilic network will generally result in slower release. Thus, release times can range from as low as 2 hours to as much as 25 hours or more, preferably the release time is at least 15 hours and especially at least 20 hours.

The network is then removed from the solution and dried, trapping a given amount of the drug. The amount of drug retained in the network and the release rate depends on the exact nature of the network.

The shape or form of the network is widely variable. The networks can be made into thin films which can act as pseudo-skin or as an implantable patch. They can also be formed into other shapes besides thin films, including, but not restricted to, small beads using techniques known in the art such as suspension polymerization or micro-emulsion polymerization, tablets for ingestion and other forms or shapes useful for implantation. Beads can then be used in either an injectable format or some other type of controlled release mechanism to go through the digestive tract.

A pharmacologically active agent is any agent or combination of agents which cause, suppress, modify, alter or otherwise cause an in vivo physiological response. Such agents include, but are not restricted to: primary medication or drugs such as insulin, B-blocking drugs, antifungal agents, antibacterial agents, and anti viral agents; agents undergoing biotransformation (those that become activated in vivo or form active metabolites) such as phenacetin, allopurinol, choral hydrate and certain tricyclic antidepressants (imipramine, amitriptyline); combination agents, agents which are active only in combination or cause synergistic effects; and any other medicinal agent. These agents, once impregnated or otherwise deposited in the network, will be released in a controlled manner as more fully described in the examples.

Of course, one of the major advantages of the network of the present invention is that the hydrophobic regime is made of elastomeric polyisobutylene. Polyisobutylene is unique in many ways from other elastomers. Key properties for the present application include, but are not restricted to, excellent oxidative and other normal degradative process stability, flex fatigue resistance and a substantially non-reactive backbone. The properties of polyisobutylene, coupled with the excellent properties of the acrylate hydrophilic segments, make the networks of the present invention ideally suited for use as drug controlled release compositions.

Throughout this specification and claims, all percentages are by weight and are based on total amphiphilic polymer network weight unless otherwise stated.

This invention will now be described in further detail with reference to the specific examples which follow.

EXAMPLES 1–10

Methacryloyl capped polyisobutylene (MA-PIB-MA) was synthesized according to the procedure described in J. P. Kennedy and M. Hiza, *Polymer Bulletin*, Vol. 10, page 146 (1983). Two batches, having number average molecular weights $M_n$ of 4,920 and 10,200, respectively, were prepared. These two macromers are designated as N-5 and N-10, respectively, hereinafter. Molecular characteristics of these macromers are shown in Table I. 2-(Dimethylamino)ethyl methacrylate was used without further purification. Isobutyronitrile (AIBN) was recrystallized from methanol. Tetrahydrofuran (THF) was distilled over calcium hydride. n-Heptane (reagent grade) was used without further purification.

TABLE I

Molecular Characteristics of MA-PIB-MAs Used For Network Synthesis

| MA-PIB-MA | $M_n$ | $M_w/M_n$ | NMR | $F_n$*  FTIR |
|---|---|---|---|---|
| N-5 | 4920 | 1.6 | 1.99 | $2.27 \pm 0.2$ |
| N-10 | 10200 | 1.7 | 2.0 | $2.0 \pm 0.2$ |

*Number average terminal functionality determined spectroscopically

Network Synthesis

Amphiphilic polymer networks were prepared in film and cube shapes. In the case of film, the copolymerization of MA-PIB-MA with DMEAMA was carried out in one ounce cylindrical bottles using AIBN initiator and THF solvent at 60° C. Before the system gelled and became unpourable, the mixture was transferred to an aluminum dish, which was then placed in an oven, protected with a nitrogen atmosphere, at 60° C. for three days to give a film with a thickness of about 1 mm.

It is important to avoid transferring the reactant mixture from the cylindrical bottle to the aluminum dish too soon, since early transfer will result in phase separation during film formation. One can determine a suitable time for transfer by running at least two samples of each composition, noting from the first the length of time for gelation to occur, and then transferring the second sample to the aluminum dish just short of that time. In the case of the cube, the polymerization charge was kept in the cylindrical bottle for three days and was then cut into cubes having sides approximately 6 mm.

To remove unreacted MA-PIB-MA, unreacted DMAEMA, and PDMAEMA homopolymer, the network was extracted sequentially with n-hexane for 24 hours, ethanol for five hours, and water for two days, all at room temperature (about 20°–25° C.).

Swelling

Swelling experiments were carried out by the use of both distilled water and n-heptane. The dried and weighed network was placed in solvent (water or n-heptane) and was then weighed periodically until a constant weight was reached. Swelling experiments were carried out at ambient temperature. The swelling curve was obtained by plotting the amount of solvent absorbed per gram of network (S/N) against time.

Analytical Techniques

Molecular weights ($M_n$ and $M_w$) of the two MA-PIB-MA macromers were determined by a Waters Associates high pressure GPC instrument (Model 6,000 A Pump, WISP 710 B Automatic Injector), a series of five $\mu$-Styragel columns ($10^5$, $10^4$, $10^3$, 500 and 100 A), Differential Refractometer 2401, and UV Absorbance Detector 440].

Figure 2:
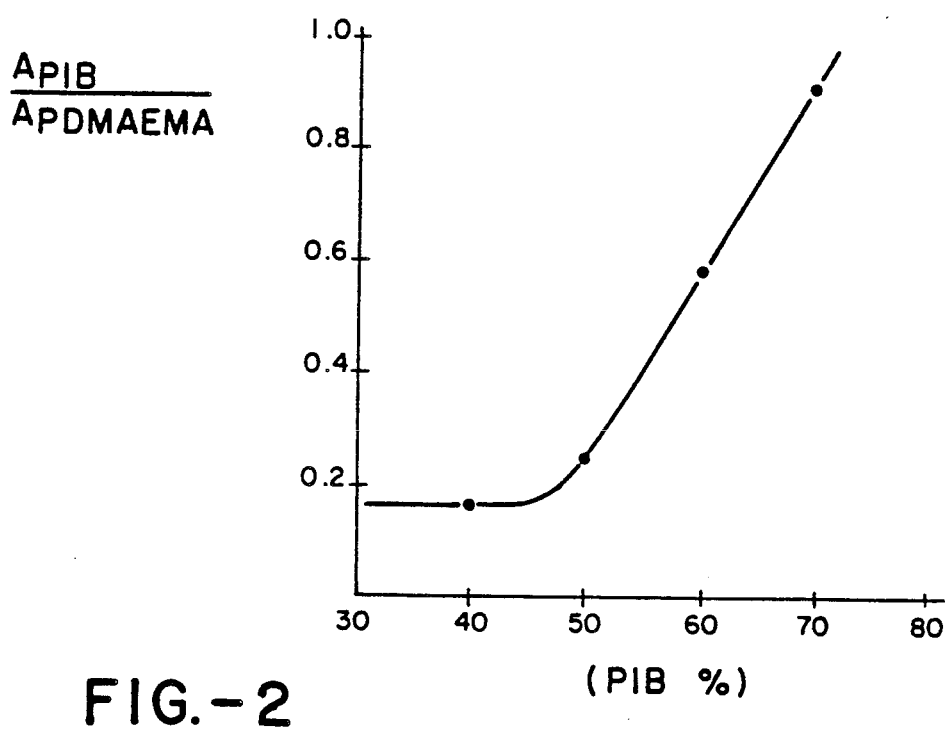
FIG. 2 is an FTIR calibration curve for preferred amphiphilic networks of the invention.

Number average terminal functionality F of the MA-PIB-MA macromers was determined spectroscopically by nuclear magnetic resonance (NMR), the latter using a Beckman FT 2100 spectrometer equipped with a Spectra Tech Model 300 ATR (attenuated total reflectance) attachment. ATR spectra were drawn with a 50 mm KRS-5 crystal at a 45· angle. A doublet at 1362 and 1400 cm$^{-1}$, due to gem-$CH_3$ groups in MA-PIB-MA, was used to quantitate the MA-PIB-MA in the network. An absorption at 2772 cm$^{-1}$, due to —$CH_2$— stretching vibration in a tertiary amine was used to quantitate the PDMAEMA content in the network. Quantities thus obtained by analysis of the networks after extraction were compared with the FTIR calibration curve shown in FIG. 2. In FIG. 2, relative absorbencies of PIB (polyisobutylene) and PDMAEMA, or more precisely, the absorbance ratio $A_{PIB}$ and $A_{PDAEMA}$, respectively, as a function of weight percentage of PIB, is shown. This calibration curve was constructed by preparing a series of networks having different compositions and analyzing the MA-PIB-MA reactant of the unextracted networks (so that network, homopolymer and unreacted monomers are still present). Unextracted networks must be used to insure that the true overall amounts of MA-PIB-MA and DMAEMA charged are obtained for calibration purposes (since the FTIR absorptions of gem-$CH_3$ groups in MA-PIB-MA and of —$CH_2$— in the tertiary amine should be the same in the network, homopolymer or unreacted monomer). As may be seen from the calibration curve in FIG. 2, sensitivity of this technique is very good at PIB contents over about 50%; however, below about 47% PIB in the network, sensitivity of this technique is unsatisfactory.

DSC analysis was carried out on a DuPont 1090 Thermal Analyzer under nitrogen at a heating rate of 20% C./min.

Stress-strain data were obtained on an Instron Universal Testing Instrument with a 5 kg load cell and 5 cm/min cross-head speed at room temperature using microdumbbell samples.

Results

Network characteristics of 10 amphiphilic polymer networks, prepared with two different MA-PIB-MA samples having $M_n$ values of 4920 and 10200, respectively, and prepared with different relative amounts of MA-PIB-MA and DMAEMA in the reactor charge (i.e., the weight of reactants charged to the reactor), are shown in Table II below. The amount of PIB in each network was obtained by comparing the absorption ratio of PIB and of DMAEMA in the network (the unknown) vs. the relative absorbencies in a mixture of known composition. In Table II, the network abbreviation code indicates an $M_n$ of MA-PIB-MA macromonomer (rounded to the closest thousand and divided by 1000) and the percentage of PIB in the network. For example, N-5-48 indicates a network prepared with MA-PIB-MA having an $M_n=4920$ and containing 48.5% PIB. Also in Table II, the average chain length $M_c$ of PDMAEMA is calculated on the assumption that all of the MA-PIB-MA enters into the network. This is not always the case, especially at higher MA-PIB-MA/DMAEM charge ratios, as shown by the relative weight percentage of extracting materials (extract) and the fact that the PIB percentage at high MA-PIB-MA/DMAEMA charge ratios may be slightly lower in the network product than in the charge.

TABLE II

Network synthesis conditions and compositions
(Copolymerizations in 7 mL THF with 0.07 g AIBN at 60° C.)

| Network | Charge MA-PIB-MA (g) | DMAEMA (g) | Ex-tract % | Network Characteristics PIB % | ** |
|---|---|---|---|---|---|
| 1 | N-5-48 | 0.6 | 1.4 | 21.4 | 48.5 | 2610 |
| 2 | N-5-51 | 0.8 | 1.2 | 26.5 | 51.0 | 2360 |
| 3 | N-5-53 | 1.0 | 1.0 | 27.1 | 53.0 | 2180 |
| 4 | N-5-61 | 1.2 | 0.8 | 29.3 | 61.0 | 1570 |
| 5 | N-5-64 | 1.4 | 0.6 | 30.5 | 64.0 | 1380 |
| 6 | N-10-49 | 0.6 | 1.4 | 20.7 | 49.5 | 5190 |
| 7 | N-10-53 | 0.8 | 1.2 | 22.4 | 53.0 | 4700 |
| 8 | N-10-56 | 1.0 | 1.0 | 23.8 | 56.3 | 3950 |
| 9 | N-10-58 | 1.2 | 0.8 | 27.3 | 58.2 | 3660 |
| 10 | N-10-71 | 1.4 | 0.6 | 35.7 | 71.5 | 2030 |

**$M_c$, PDMAEMA calculated; for assumptions - see text

Figure 3:
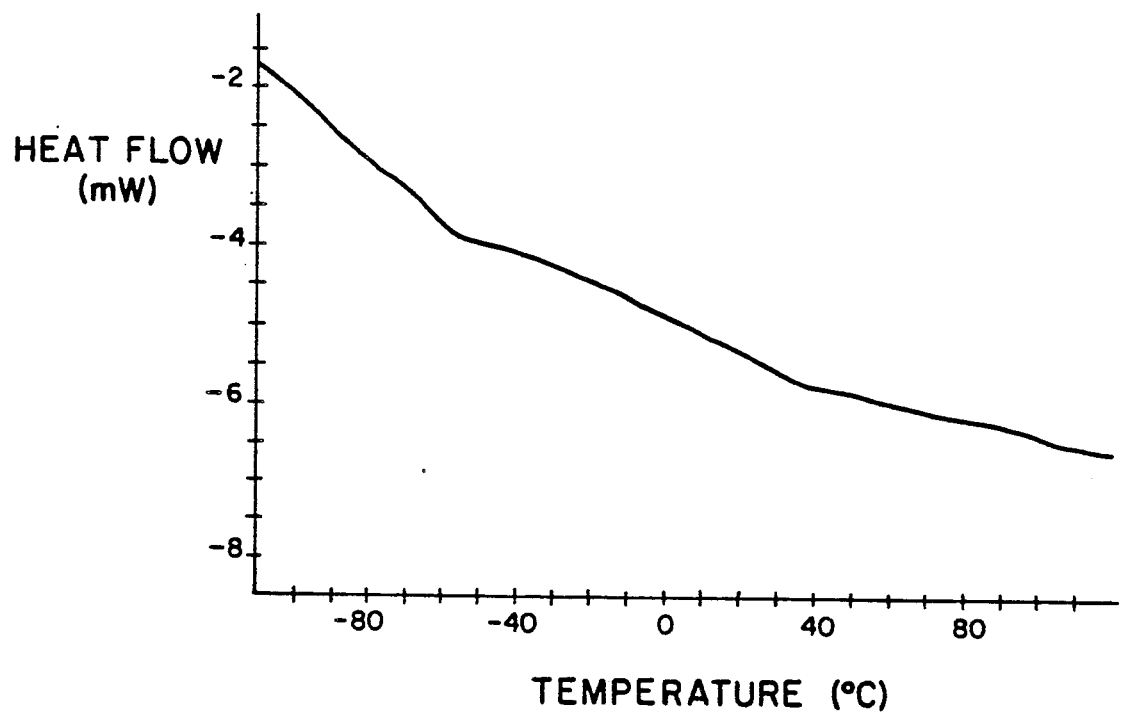
FIG. 3 is an DSC trace of a representative amphiphilic network prepared according to this invention.

DSC Trace of Amphiphilic Network N-10-56 (prepared in Example 8) is shown in FIG. 3 and given in Table III. This trace shows heat flow in milliwatts (mW) as a function of temperature. The negative signs denote heat outflow. The network exhibits two glass transition temperatures ($T_g$), one at $-60°$ C. and one at $30°$ C., indicating phase segregation into PIB ($T_g = -73°$ and PDMEMA ($T_g = 19°$ C.) domains. The higher than literature $T_g$ values may be due to the relatively fast rate of heating used herein (20° C./min) or to the restricted motion of the network chain segment.

TABLE III

DSC Trace of Amphiphilic Network N-10-56
(Example 8)

| Temp.,° C. | Heat Flow, mW |
|---|---|
| −110 | −1.8 |
| −60 | −4.0 |
| +30 | −5.5 |
| +120 | −6.5 |

Figure 4:
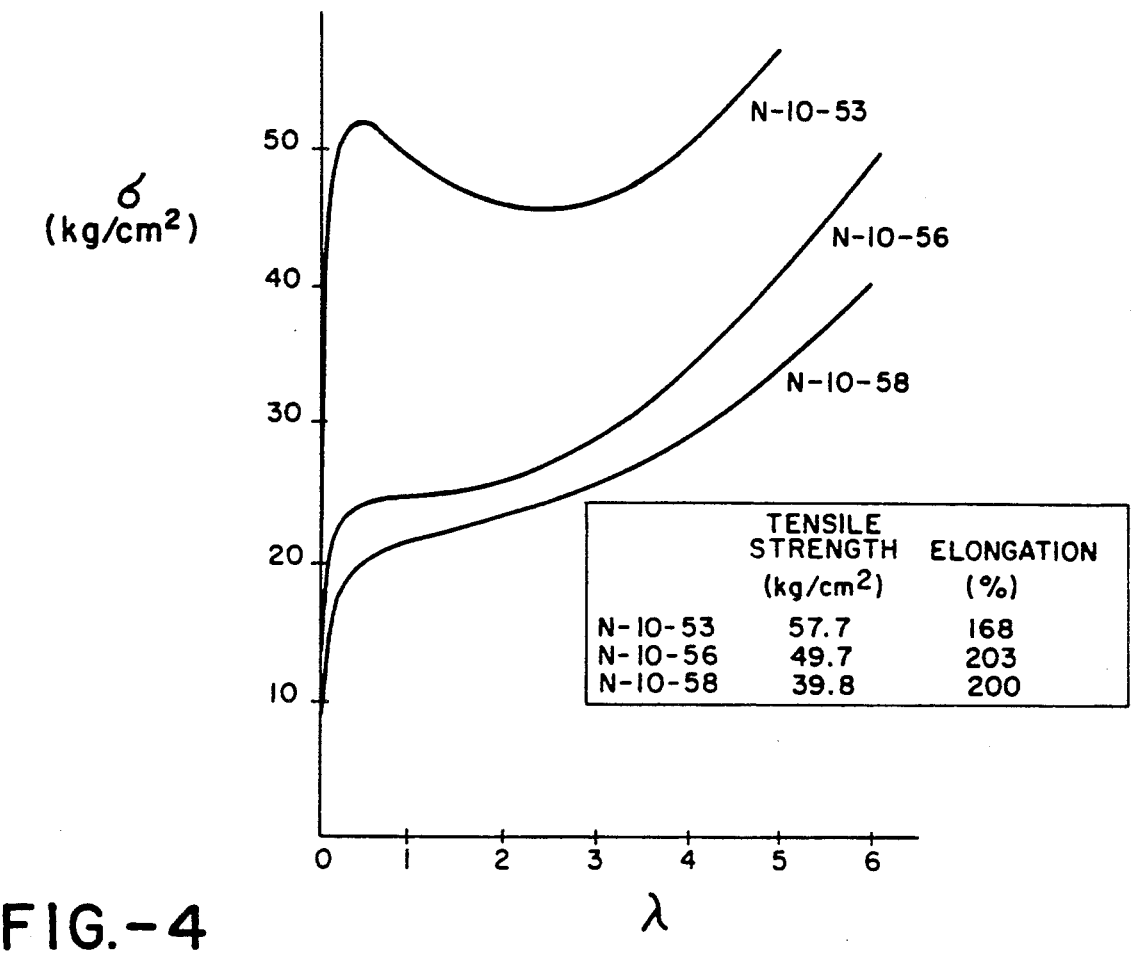
FIG. 4 is a series of stress/strain curves of amphiphilic networks of this invention.

Mechanical properties of three amphiphilic polymer networks (those of Examples 7, 8 and 9) are given in Table IV and shown in FIG. 4. Table IV gives tensile strength (in kilograms per square centimeter) and percentage elongation (both at break) of these networks, while FIG. 4 shows the stress-strain curves of these networks. The networks were oven-dried at 60° C. under nitrogen atmosphere for 25 hours before the stress/strain curves were run.

As is apparent from FIG. 4, network N-10-53 (Example 7) has a stress-strain curve with an essentially linear region of high modulus at low elongation, a yield point (at a stress of about 52 kg/cm² and an elongation of about 50%), and a non-linear region including a retrograde slope at higher elongations. The other two networks, having larger PIB contents, did not exhibit yield points. These curves show the tensile strength increases at percentage elongation at break decreases (generally) with increasing PDMAEMA content, although there was little difference in elongation at break between networks N-10-56 and N-10-58.

TABLE IV

Stress-Strain Curves of Amphiphilic Networks

| Example | Network | Tensile Strength (Kg/cm²) | Elongation % |
|---|---|---|---|
| 7 | N-10-53 | 57.7 | 168 |
| 8 | N-10-56 | 49.7 | 203 |
| 9 | N-10-58 | 39.8 | 200 |

FIGS. 5–8 show the extent of swelling of amphiphilic networks of this invention in water and n-heptane. The degree of swelling, S/N, is shown as a function of time. The degree of swelling, S/N, represents the incremental volume (S) divided by the original volume (N) of the network before imbibition of water.

Figure 5:
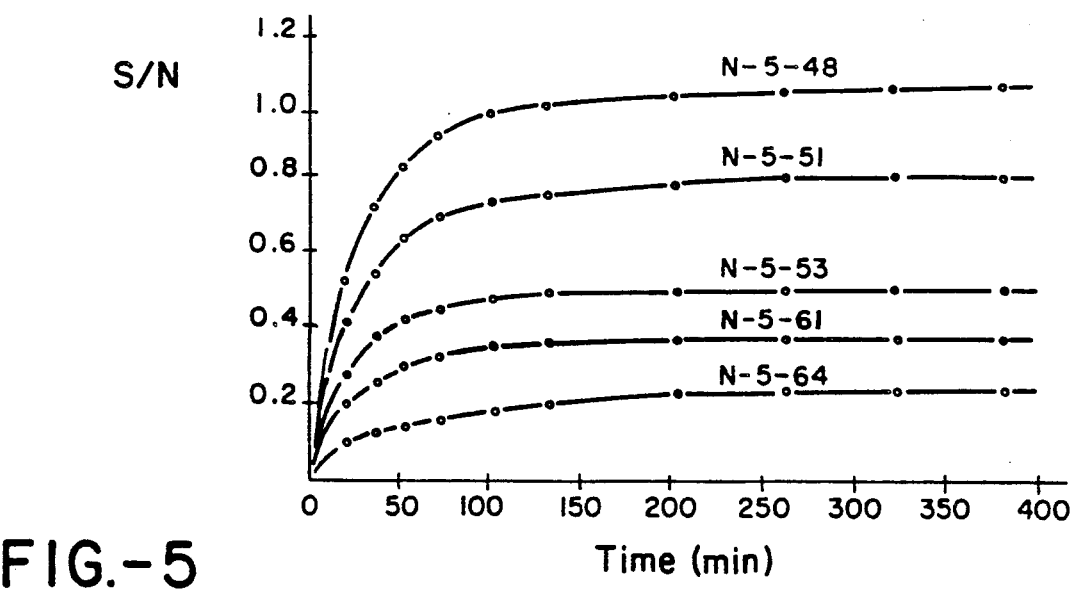

FIG. 5 show the extent of swelling of the amphiphilic networks of Examples 1–5 in water.

FIG. 6 show the swelling of the amphiphilic networks of Examples 6–10 in water.

Figure 8:
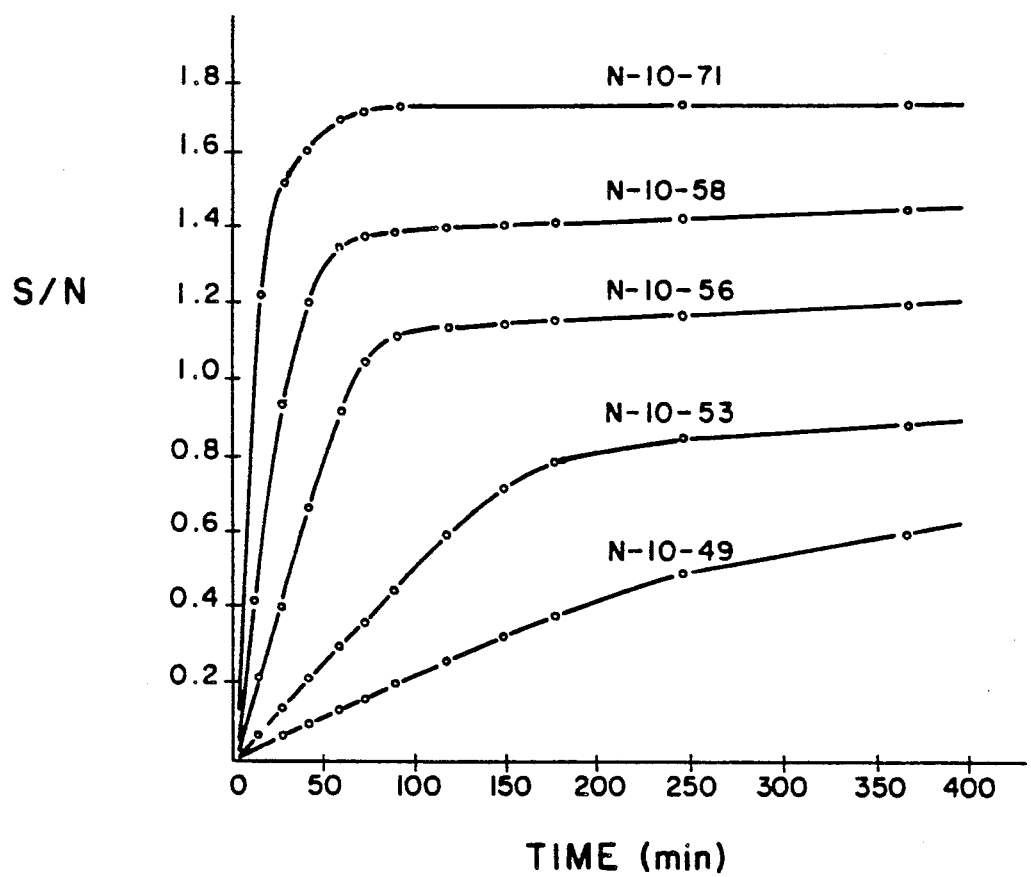

FIGS. 7 and 8, show swelling of amphiphilic networks in n-heptane at room temperature. Data for the amphiphilic networks of Examples 1–5 are given in FIG. 7; data for the networks of Examples 6–10 are given FIG. 8.

All of the amphiphilic networks exhibited an equilibrium degree of swelling, as shown by the fact that there is virtually no change in volume after 210 minutes. As the data in FIGS. 5–8 show, swelling in water decreases and swelling in n-heptane increases with increasing PIB content.

EXAMPLE 11

Radical copolymerization of MA-PIB-MA with DMAAm in THF was carried out in closed teflon molds under nitrogen in a DN-43HI Inert Oven (Scientific Products). Experimental data and conditions are given in Table V. The network abbreviation codes of the resulting materials indicate the $M_n$ of the starting MA-PIB-MA (divided by 1,000) and the weight percent of PIB obtained by elemental analysis in the network. DSC analysis was carried out on a DuPont 1090 thermal analyzer under nitrogen at a 20° C./min heating rate. Networks were loaded with theophylline in swelled state in saturated water solution for three days followed by drying until constant weight was reached. Release studies were carried out in distilled water and theophylline was monitored by UV spectroscopy.

TABLE V

Experimental conditions for the synthesis of amphiphilic networks composed of PDMAAm-l-PIB

| Sample | PIB (g) | MA End Group (mol 10⁴) | DMAAm (g) | DMAAm (mol 10²) | AIBN (mol 10⁵) |
|---|---|---|---|---|---|
| A-4-26 | 0.6 | 3.08 | 1.4 | 1.41 | 3.11 |
| A-4-45 | 0.8 | 4.10 | 1.2 | 1.21 | 2.13 |
| A-4-56 | 1.0 | 5.13 | 1.0 | 1.01 | 1.52 |
| A-4-59 | 1.2 | 6.15 | 0.8 | 0.81 | 1.04 |
| A-4-77 | 1.4 | 7.18 | 0.6 | 0.61 | 0.73 |
| A-9.5-31 | 0.6 | 1.26 | 1.4 | 1.41 | 1.62 |
| A-9.5-40 | 0.8 | 1.68 | 1.2 | 1.21 | 1.17 |
| A-9.5-49 | 1.0 | 2.11 | 1.0 | 1.01 | 0.84 |
| A-9.5-59 | 1.2 | 2.53 | 0.8 | 0.81 | 0.52 |
| A-9.5-76 | 1.4 | 2.95 | 0.6 | 0.61 | 0.32 |

A-4 series, THF solvent, total volume 10 mL
A-9.5 series, THF solvent, total volume 8 mL
Reaction time 72 hours
Reaction temperature 60° C.

TABLE VI

Characterization of the PDMAAm-l-PIB amphiphilic networks

| Sample | % Extract Hexane | % Extract Ethanol | PIB Phase Tg °C. | PDMAAm Phase Tg °C. |
|---|---|---|---|---|
| A-4-26 | 5.7 | 1.8 | −61 | 104 |
| A-4-45 | 6.3 | 3.2 | −54 | 102 |
| A-4-56 | 9.3 | 1.4 | −54 | 94 |
| A-4-59 | 8.2 | 2.1 | −53 | 90 |
| A-4-77 | 1.8 | 0.8 | −52 | ND |
| A-9.5-31 | 5.2 | 18.6 | −63 | 115 |
| A-9.5-40 | 4.9 | 11.9 | −62 | 110 |
| A-9.5-49 | 3.1 | 6.6 | −60 | 108 |
| A-9.5-59 | 1.4 | 5.4 | −59 | 95 |
| A-9.5-76 | 1.5 | 2.5 | −58 | ND |

Tg of PIB ($M_n = 9,500$): −65° C.
TG of PIB ($M_n = 4,000$): −69° C.
Tg of Poly(N,N-dimethylacrylamide): 112° C.
ND = not determinable Tables V and VI summarize synthesis conditions, data obtained by extraction and DSC, respectively. On the basis of the results of orienting experiments, the AIBN concentrations were kept relatively low and changed in order to provide sufficiently high kinetic chain length (v) during copolymerization of DMAAm and MA-pIB-MA. Since $v \sim [M]/[I]^{\frac{1}{2}}$ this relationship governed the experimental design. As exhibited in Table VI, the amount of extractables are below 10% in most of the cases. This indicates high polymerization yields and nearly exact network formation. When detectable, two $T_g$'s appeared in the DSC curves as listed in Table VI. This finding is due to microphase separation of hydrophobic and hydrophilic segments in these transparent materials.

Figure 9:
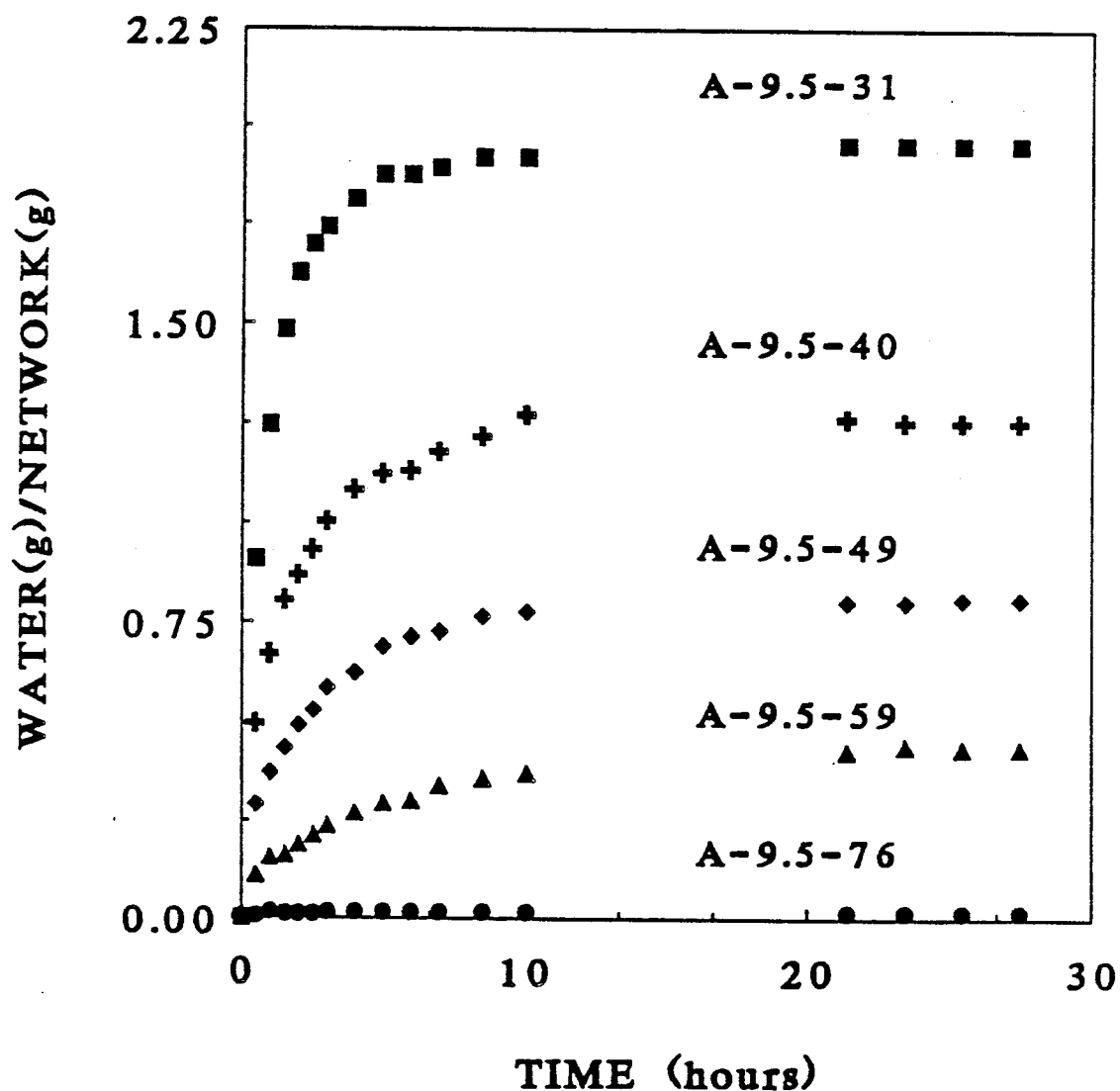
FIG. 9 is a series of swelling curves of five representative amphiphilic networks of this invention in water at room temperature when the hydrophilic acrylate is N,N-dimethylacrylamide.
Figure 10:
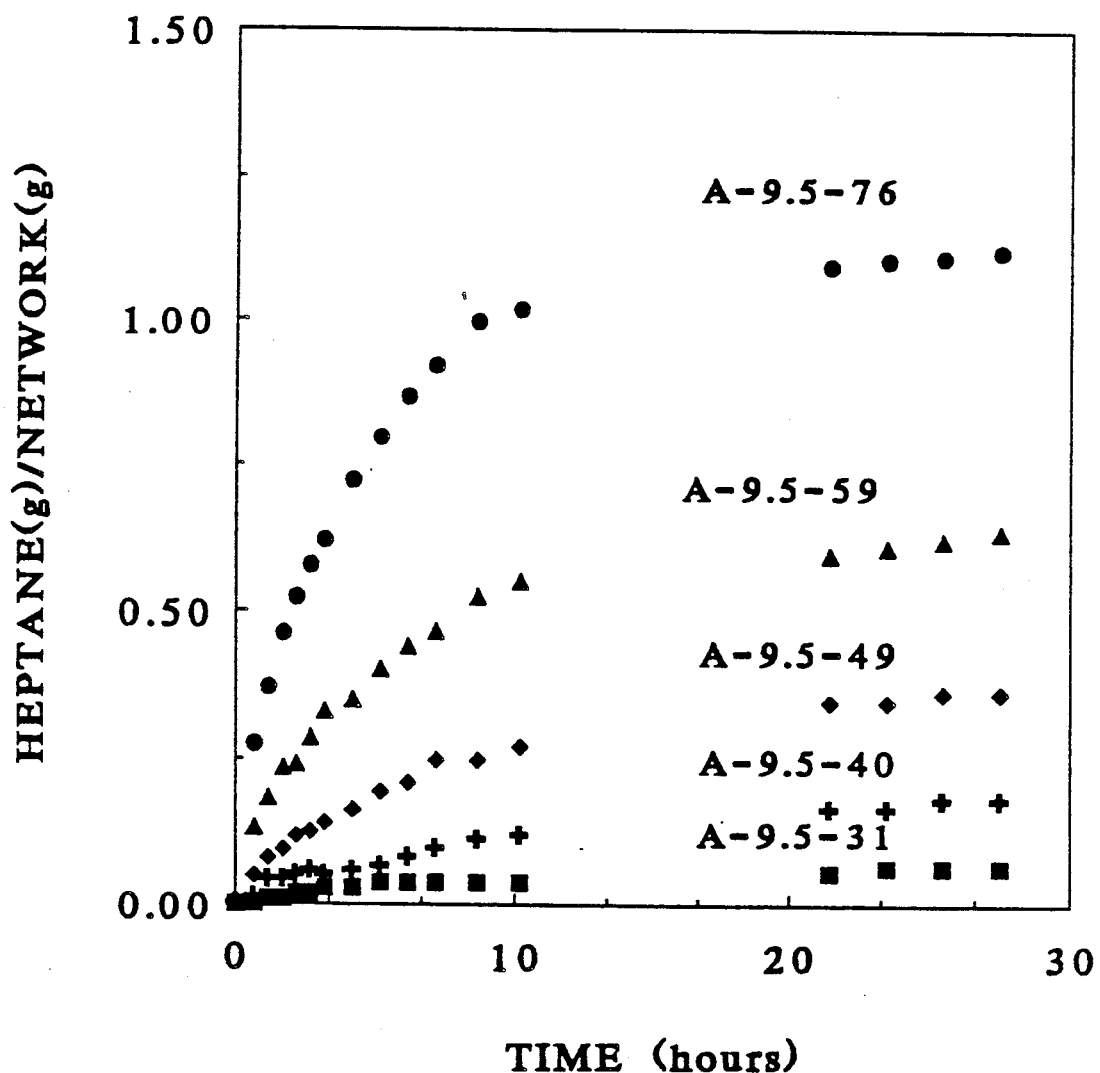
FIG. 10 is a series of swelling curves analogous to FIG. 9 except that the swelling is done in heptane at room temperature.

The amphiphilic nature of the PDMAAm-l-PIB networks was substantiated by swelling studies. Amphiphilic networks are expected to swell both in hydrophilic and hydrophobic solvents. FIGS. 9 and 10 show the amount of solvent absorbed per gram network vs. time plots for a series of networks ($M_n$(PIB)=9,500) in water and in n-heptane, respectively. As these figures exhibit, the degree of swelling changes significantly with changes in network composition. Thus, the degree of swelling in water decreases with increasing PIB content, e.g. swelling decreases from 190% to nearly zero by increasing the PIB content from 31% to 75%. Similar to the swelling in water, the degree of swelling in D-heptane changes with network composition but in a reverse order, i.e., the maximum degree of swelling increases as PIB content increases.

Figure 11:
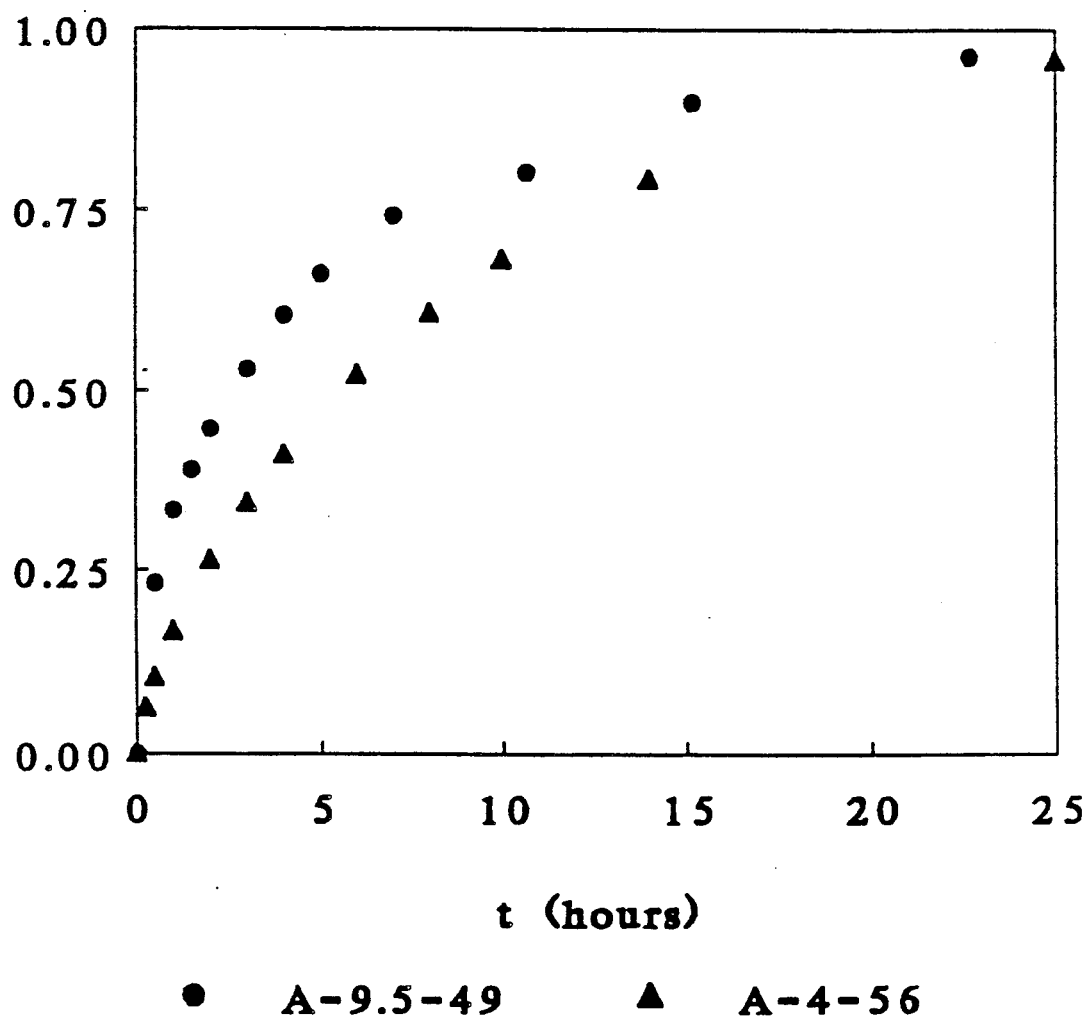
FIG. 11 is a plot of the release profile of theophylline in two representatives amphiphilic networks from FIG. 9 and Table V.

FIG. 11 shows the release curve of the theophylline, i.e., the amount of drug released at time t ($M_t$) over the total amount $M_w$ in the network, $M_t/M_w$ as a function of time, from networks A-4-56 and A-9.5-49. As exhibited in the figure, loading of PDAAm-l-PIB amphiphilic networks with theophylline yields slowly releasing drug delivery systems, i.e., relatively long time, 24 hours, is necessary for nearly complete release of the drug.

The release kinetics, the rate and type of release from sustained drug delivery systems can be analyzed by the use of $M_t/M_w = kt^n$ expression. In the case of pure Fickian diffusion, n=0.5 whereas n=1 indicated zero-order release. As shown in FIG. 12, n can be obtained from the log ($M_t/M_w$) versus log t plots. With the A-9.5-49 sample n=0.47 indicates that the release of theophylline is controlled by diffusion, while n=0.67 in the case of the A-4-56 sample suggests that the release kinetics can be altered by the $M_n$ of the PIB.

EXAMPLE 12

HEMA was protected prior to polymerization with MA-PIB-MA by the dropwise addition of trimethylsilylchloride (Cl-TMS) to HEMA in the presence of triethylamine acid acceptor. The reaction was carried out in THF at 0° C. and stirred overnight. The triethylamine hydrochloride was removed by filtration and the THF evaporated. The 2-(trimethylsiloxy)ethyl methacrylate (TMSHEMA) was purified by column chromatography and the purity determined to be 99% by GC.

Network synthesis

Radical copolymerization of MA-PIB-MA and TMSHEMA in THF was carried out in closed teflon molds under nitrogen in a DN-43HI inert oven (Scientific Products). Experimental data and conditions are given in Table VII. The network abbreviation codes represent the comonomer HEMA (H), the $M_n$ of the starting MA-PIB-MA divided by 1,000 and the weight percent of the MA-PIB-MA in the reaction charge respectively. The networks were removed from the mold after polymerization and the THF allowed to evaporate. The deprotection reaction was accomplished by swelling the networks in a 5% solution of HCl in 2-methoxyethanol for three days. The HCl solution was changed daily to facilitate the reaction. The networks were then extracted with ethanol and hexane for 24 hours each concurrently.

Network Characterization

The networks were characterized by DSC on a DuPont 1090 thermal analyzer under nitrogen at a heating rate of 20° C./min. The samples were preheated to 130° C., equilibrated for 10 minutes and then cooled to room temperature at 1° C./min prior to the experiment. The swelling properties were determined in D-heptane at room temperature and water at 37° C.

Release experiments

Networks H-4-50 and H-9.5-50 were loaded with theophylline by soaking them in a saturated water solution for three days. The solution was maintained at saturation by adding additional theophylline as needed. The networks were then dried to constant weight in a vacuum oven. Release studies were carried out in distilled water and the theophylline was monitored by UV spectroscopy at 274 nm absorption maximum. The distilled water was replaced periodically to ensure infinie sink conditions. Theophylline was recrystallized from water prior to the loading.

TABLE VII

Experimental conditions for the synthesis of amphiphilic networks composed of PHEMA-l-PIB

| Sample | PIB (g) | MA End Group (mol $10^4$) | HEMA (g) | HEMA (mol $10^3$) | TMS HEMA (g) | AIBN (mol $10^5$) |
|---|---|---|---|---|---|---|
| H-4-30 | 0.6 | 3.08 | 1.4 | 10.76 | 2.18 | 1.66 |
| H-4-40 | 0.8 | 4.10 | 1.2 | 9.22 | 1.87 | 1.18 |
| H-4-50 | 1.0 | 5.13 | 1.0 | 7.68 | 1.55 | 0.86 |
| H-4-60 | 1.2 | 6.15 | 0.8 | 6.15 | 1.24 | 0.54 |
| H-4-70 | 1.4 | 7.18 | 0.6 | 4.61 | 0.93 | 0.32 |
| H-9.5-30 | 0.6 | 1.26 | 1.4 | 10.76 | 2.18 | 1.62 |
| H-9.5-40 | 0.8 | 1.68 | 1.2 | 9.22 | 1.87 | 1.15 |
| H-9.5-50 | 1.0 | 2.11 | 1.0 | 7.68 | 1.55 | 0.84 |
| H-9.5-60 | 1.2 | 2.53 | 0.8 | 6.15 | 1.24 | 0.53 |

TABLE VII-continued

Experimental conditions for the synthesis of amphiphilic networks composed of PHEMA-l-PIB

| Sample | PIB (g) | MA End Group (mol $10^4$) | HEMA (g) | HEMA (mol $10^3$) | TMS HEMA (g) | AIBN (mol $10^5$) |
|---|---|---|---|---|---|---|
| H-9.5-70 | 1.4 | 2.95 | 0.6 | 4.16 | 0.93 | 0.31 |

THF solvent, total volume 8 mL
Reaction time 72 hours
Reaction temperature 60° C.

TABLE VIII

Characterization of the PHEMA-l-PIB amphiphilic networks

| Sample | % Extract Hexane | PIB Phase Tg °C. | PHEMA Phase Tg °C. |
|---|---|---|---|
| H-3-30 | 0.8 | −61 | 107 |
| H-4-40 | 1.2 | −59 | 106 |
| H-4-50 | 1.6 | −57 | 104 |
| H-4-60 | 2.1 | −55 | 98 |
| H-4-70 | 2.1 | −54 | 100 |
| H-9.5-30 | 0.8 | −61 | 111 |
| H-9.5-40 | 1.1 | −60 | 111 |
| H-9.5-50 | 1.3 | −58 | 107 |
| H-9.5-60 | 1.7 | −57 | 107 |
| H-9.5-70 | 2.6 | −58 | 105 |

Tg of PIB (Mn = 9,500): −65° C.
Tg of PIB (Mn = 4,000): −69° C.
Tg of Poly(2-hydroxyethyl methacrylate): 110° C.
Tg of Poly(2-trimethylsilylhydroxyethyl methacrylate): 22° C.

Table VII summarizes the synthetic conditions. The amount of TMSHEMA used in each reaction was determined by the amount of HEMA that was required for a desired composition. The AIBN concentratios were kept relatively low to insure an adequate kinetic chain length during the copolymerization for network formation The networks formed are transparent, nonporous gels. Deprotection of the networks were modeled on both monomer and homopolymer. The reaction with both the monomer and homopolymer was instantaneous as determined by GC and NMR respectively. The homopolymer reaction was allowed to run for four days without any detectable ester hydrolysis. The deprotection reaction on the networks themselves was observed to be complete by following a distinct swelling front that disappeared upon completion. As exhibited in Table VIII, the amount of hexane extractable material is less than 3% in all cases. This indicates high polymerization yields and near exact network formation. The ethanol extractable material was not determined because the presence of the deprotection reaction products gives a falsely high percent of extractable material.

DSC measurements were conducted and the results appear in Table VIII. The presence of the two Tgs indicates that these materials have a microphase separated morphology. Although these materials are phase separated, they remain transparent. The Tg of the HEMA phase occurs at practically the same temperature as that of the homopolymer, indicating a complete deprotection of the network.

Figure 13:
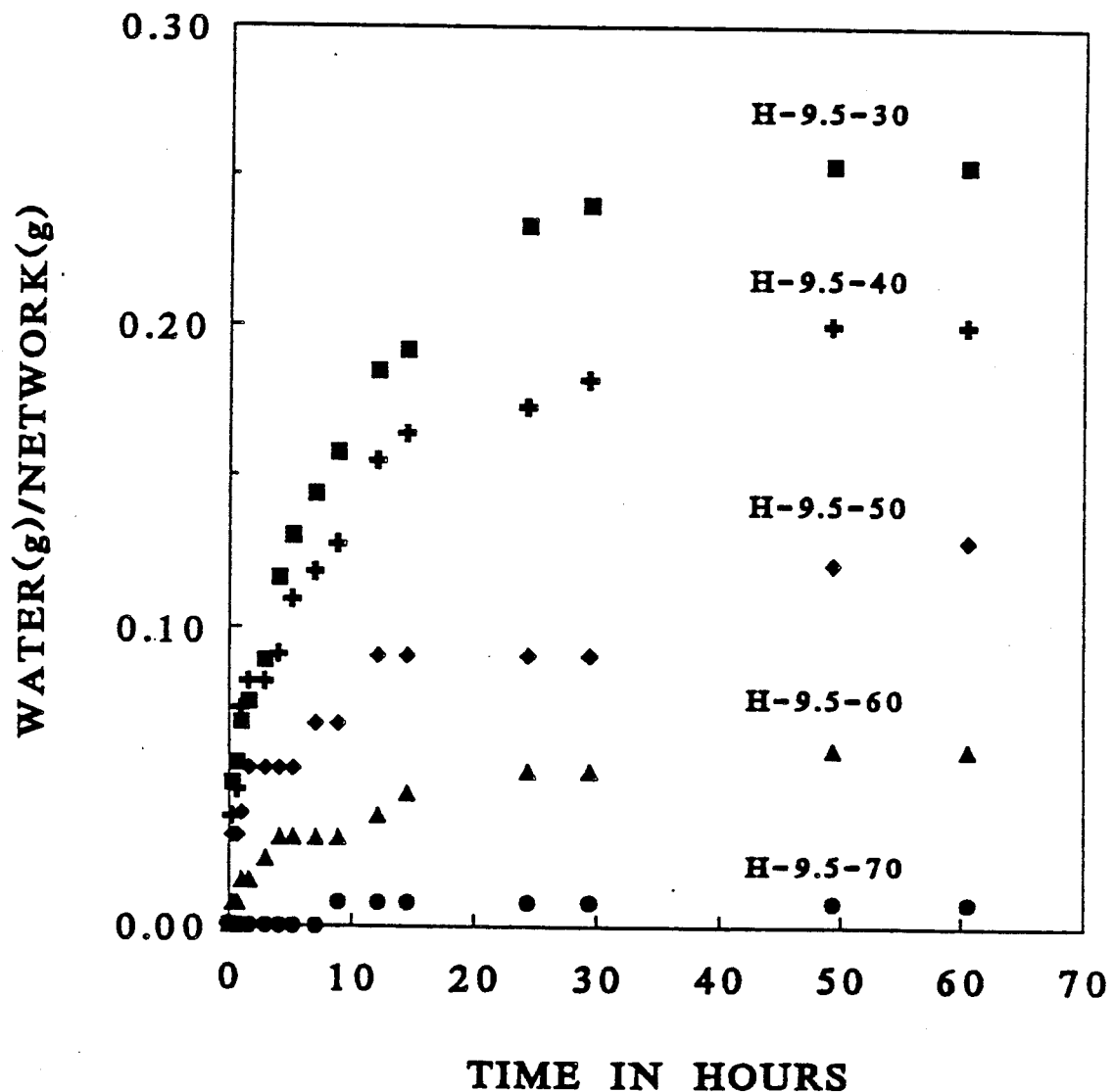
FIG. 13 is a series of swelling curves of five representative amphiphilic networks of this invention in water at room temperature, over a 70 hour time span when the hydrophilic acrylate is 2-hydroxyethylmethyl methacrylate.
Figure 14:
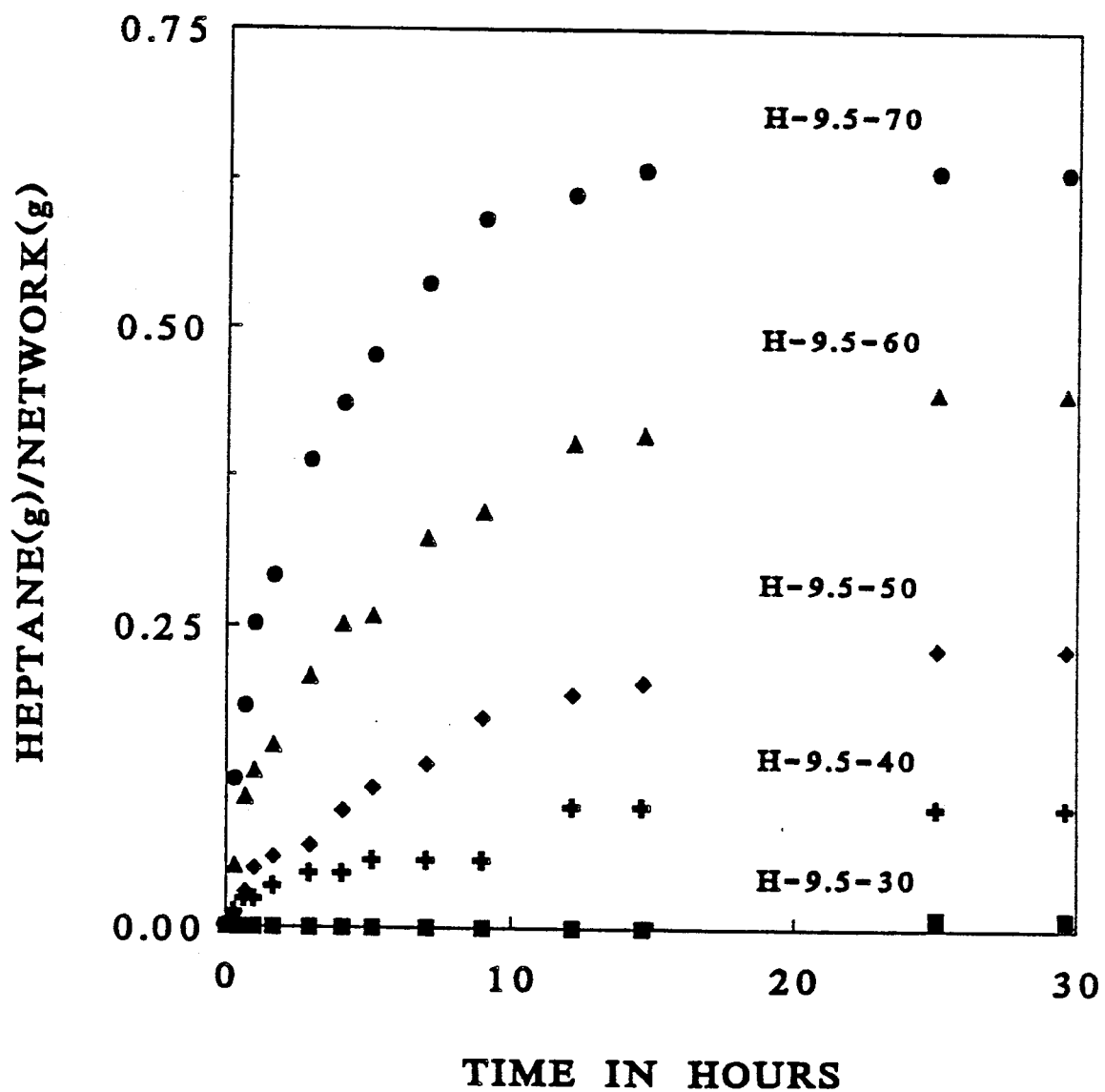
FIG. 14 is a series of swelling curves analogous to FIG. 13 except the swelling is done in heptane at room temperature.

The amphiphilic nature of the PHEMA-l-PIB networks was substantiated by swelling studies. Amphiphilic networks are expected to swell in both hydrophilic and hydrophobic solvents. FIGS. 13 and 14 show the amount of solvent absorbed per gram of network, versus time, for a series of networks ($M_n$ (PIB)=9,500) in water and in n-heptane, respectively. As can be seen in the figures, the degree of swelling changes significantly with network composition. The degree in swelling decreases from 25% for H-9.5-70 to 1% for H-9.5-70 by increasing the PIB content in the preparation from 30% to 70%. Conversely, the degree of swelling in n-heptane is greatest for H-9.5-70 and least for H-9.5-30. Therefore, the swelling of these materials is compositionally dependent.

Figure 15:
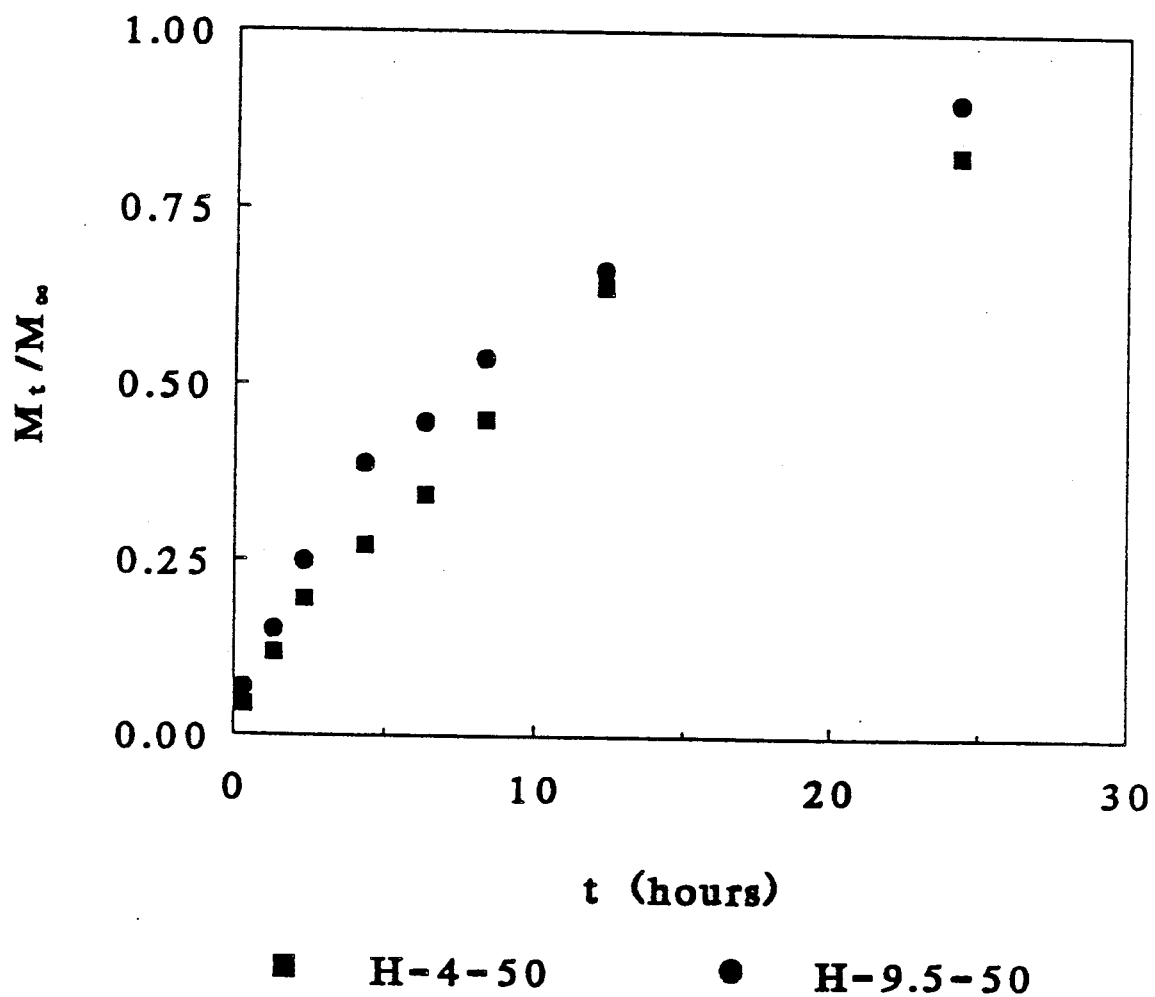
FIG. 15 is a plot of the release profile of theophylline in two representatives amphiphilic networks from FIG. 13 and Table VII.

FIG. 15 shows the fraction release of the drug versus time for networks H-4-50 and H-9.5-50. As illustrated in this figure, the theophylline loaded systems provide a delivery system capable of delivering the drug for an extended period of time. The release kinetics and the mechanism of release for the delivery system can be analyzed by applying the equation $M_t/M_w = kt^n$. In the case of n=0.5 the release mechanism is Fickian diffusion whereas in the case of n>0.5 a process in addition to diffusion is taking place which is known as anomalous transport. For the special case of n=1, a polymer relaxation controlled transport occurs known as Case II transport. This is of particular interest because the drug release from such a device can be zero order.

As shown in FIG. 16, n can be obtained from the slope of the ln ($M_t/M_w$) versus ln t plots. Release from networks H-4-50 and H-9.5-50 results in a value of n=0.72 and n=0.65 respectively, indicating anomalous diffusion in both cases. These results suggest that the release kinetics can be altered by the $M_n$ of the MA-PIB-MA employed in the synthesis.

While in accordance with the patent statutes the best mode and preferred embodiment of the invention have been described, it is to be understood that the invention is not limited thereto, but rather is to be measured by the scope and spirit of the appended claims.

What is claimed is:

1. A controlled and/or sustained drug release, amphiphilic composition comprising:
   a network having hydrophobic segments and hydrophilic segments and impregnated with a pharmaceutically active agent;
   wherein said hydrophobic segment is an acryloyl or methacryloyl capped polyolefin or mixture thereof and said hydrophilic segment is a polyacrylate derived from an acrylate selected from the class consisting of formulas (II), (III) and (IV)

$$H_2C=C(R^2)-C(=O)-O-R^3-N(R^4)(R^5) \quad (II)$$

$$H_2C=C(R^2)-C(=O)-N(R^4)(R^5) \quad (III)$$

$$H_2C=C(R^2)-C(=O)-O-R^3-OH \quad (IV)$$

where $R^2$ is hydrogen or methyl, $R^3$ is an alkylene group of 2 to about 4 carbon atoms, and $R^4$ and $R^5$ may be the same or different and each is hydrogen or an alkyl radical of 1 to about 4 carbon atoms.

2. A composition according to claim 1 characterized by the ability to absorb, on a weight basis, about 0% to about 200% by weight of water and about 0% to about 170% by weight of n-heptane.

3. A composition according to claim 1, said composition having two glass transition temperatures.

4. A composition according to claim 1 in which said polyolefin is a polymer of an olefin monomer containing from 4 to 10 carbon atoms.

5. A composition according to claim 4 in which the olefin monomer is isobutylene.

6. A composition according to claim 1 in which said hydrophobic polyolefin is methacryloyl capped.

7. A composition according to claim 1 wherein said hydrophilic segment is polyacrylate derived from a acrylate of formula (IV).

8. A composition according to claim 7 wherein said acrylate is 2-(hydroxy)ethyl methacrylate (HEMA).

9. A composition according to claim 2 characterized by the ability to absorb, on a weight basis, about 20% to about 170% by weight of water and about 20% to about 170% by weight of n-heptane.

10. A composition according to claim 9 characterized by the ability to absorb, on a weight basis, about 40% to about 120% by weight of water and about 40% to about 120% by weight of n-heptane.

11. A composition according to claim 1 characterized by an exponential factor n having a value from about 0.4 to about 1.0.

12. A composition according to claim 11 wherein n is from about 0.45 to about 0.8.

13. A composition according to claim 1 characterized by having a release time of at least 2 hours.

14. A composition according to claim 13 wherein said time is at least 20 hours.

15. A composition according to claim 1 consisting essentially of a polymer product of (a) about 20% to about 75% by weight of a hydrophobic methacryloyl capped polyisobutylene and (b) about 80% to about 25% by weight of hydrophilic 2-(hydroxy)ethyl methacrylate, based on total polymer weight.

16. An amphiphilic polymer network according to claim 15, said network consisting essentially of the product of (a) about 35% to about 65% by weight of said hydrophobic methacryloyl capped polyisobutylene and (b) about 65% to about 35% by weight of said hydrophilic 2-(hydroxy)ethyl methacrylate, based on total polymer weight.

* * * * *